(12) United States Patent
Yang et al.

(10) Patent No.: US 10,899,741 B2
(45) Date of Patent: Jan. 26, 2021

(54) 3,4-BIPYRIDYL PYRAZOLE DERIVATIVE, AND PREPARATION METHOD THEREFOR AND MEDICAL APPLICATION THEREOF

(71) Applicants: Jiangsu Hengrui Medicine Co., Ltd., Jiangsu (CN); Shanghai Hengrui Pharmaceutical Co., Ltd., Shanghai (CN)

(72) Inventors: Fanglong Yang, Shanghai (CN); Ling Zhang, Shanghai (CN); Guangyuan Shen, Shanghai (CN); Feng He, Shanghai (CN); Weikang Tao, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 16/349,165

(22) PCT Filed: Nov. 13, 2017

(86) PCT No.: PCT/CN2017/110686
§ 371 (c)(1),
(2) Date: May 10, 2019

(87) PCT Pub. No.: WO2018/086609
PCT Pub. Date: May 17, 2018

(65) Prior Publication Data
US 2019/0270724 A1 Sep. 5, 2019

(30) Foreign Application Priority Data

Nov. 14, 2016 (CN) .......................... 2016 1 0998317

(51) Int. Cl.
C07D 401/14 (2006.01)
A61P 35/00 (2006.01)
C07D 405/14 (2006.01)

(52) U.S. Cl.
CPC ............ *C07D 401/14* (2013.01); *A61P 35/00* (2018.01); *C07D 405/14* (2013.01)

(58) Field of Classification Search
CPC .................................................. C07D 401/14
USPC ........................................................ 514/333
See application file for complete search history.

(56) References Cited

U.S. PATENT DOCUMENTS

| | | | |
|---|---|---|---|
| 5,859,215 A * | 1/1999 | Rodriguez-Ubis | ................ C07D 401/14 424/9.34 |
| 8,993,615 B2 * | 3/2015 | Zack | ............ A61K 31/00 514/414 |

FOREIGN PATENT DOCUMENTS

| | | |
|---|---|---|
| KR | 20160025776 | 3/2016 |
| WO | WO 2002066462 | 8/2002 |
| WO | WO 2004013135 | 2/2004 |
| WO | WO 2004026306 | 4/2004 |
| WO | WO 2004111046 | 12/2004 |
| WO | WO 2009062990 | 5/2009 |
| WO | WO 2009093029 | 7/2009 |
| WO | WO 2009151991 | 12/2009 |
| WO | WO 2012000595 | 1/2012 |
| WO | WO 2012002680 | 1/2012 |
| WO | WO 2013009140 | 1/2013 |
| WO | WO 2013056070 | 4/2013 |
| WO | WO 2014049133 | 4/2014 |
| WO | WO 2016021192 | 2/2016 |
| WO | WO 2016034134 | 3/2016 |
| WO | WO 2016106266 | 6/2016 |
| WO | WO 2017141927 | 8/2017 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802.*
Venkatesh, J. Pharm. Sci. 89, 145-154 (2000) (p. 146, left column).*

(Continued)

*Primary Examiner* — Nizal S Chandrakumar
(74) *Attorney, Agent, or Firm* — Fish & Richardson P.C.

(57) ABSTRACT

The present invention relates to a 3,4-bipyridyl pyrazole derivative, and a preparation method therefor and a medical application thereof. Specifically, the present invention relates to a new 3,4-bipyridyl pyrazole derivative as shown in formula (I), a preparation method for the derivative, a pharmaceutical composition containing the derivative, a use of the derivative as a therapeutic agent, in particular as a TGF-β inhibitor, and a use of the derivative in the preparation of a drug which treats, prevents or reduces cancer mediated by TGF-β overexpression. The substituents in formula (I) have the same definitions as in the description.

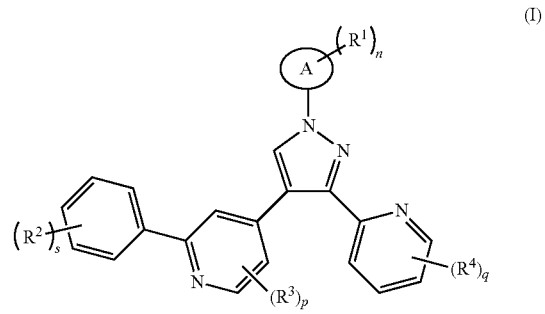

10 Claims, 1 Drawing Sheet

(56) References Cited

OTHER PUBLICATIONS

Dorwald F. A. Side Reactions in Organic Synthesis, 2005, Wiley: VCH, Weinheim p. IX of Preface p. 1-15.*
Alexandrow et al., "Transforming Growth Factor fi and Cell Cycle Regulation", Cancer Res. 55: 1452-1457, 1995.
Bitzer et al., "Transforming Growth Factor—in Renal Disease", Kidney Blood Press. Res. 21• 1-12, 1998.
Border et al., "Suppression of experimental glomerulonephritis by antiserum against transforming growth factor B1", Nature 346: 371-374, 1990.
Hojo et al., "Cyclosporine induces cancer progression by a cell-autonomous mechanism", Nature 397: 530-534, 1999.
International Preliminary Report in International Application No. PCT/CN2017/110686, dated May 14, 2019, 8 pages.
Kottler et al., "Comparative effects of TGF-b 1 and TGF-b2 on extracellular matrix production, proliferation, migration, and collagen contraction of human Tenon's capsule fibroblasts in pseudoexfoliation and primary open-angle glaucoma", Exp. Eye Res. 80: 121-134, 2005.
Maehara et al., "Role of Transforming Growth Factor-b1 in Invasion and Metastasis in Gastric Carcinoma", J Clin. Oncol. 17: 607-614, 1999.
Massague, "The Transforming Growth Factor-B Family", J. Ann. Rev, Cell. Biol. 6: 594-641, 1990.
McCaffrey et al., "Decreased Type I1/Type I TGF-B Receptor Ratio in Cells Derived from Human Atherosclerotic Lesions", J Clin. Invest. 96: 2667-2675, 1995.
Picht et al., "Transforming growth factor $\beta 2$ levels in the aqueous humor in different types of glaucoma and the relation to filtering bleb development", Graefes Arch. Clin. Exp. Ophthalmol 239: 199-207, 2001.
Picon et al., "A Subset of Metastatic Human Colon Cancers Expresses Elevated Levels of Transforming Growth Factor B1", Cancer Epidemiol. Biomarkers Prev. 7: 497-504 , 1998.
Roberts et al., "Physiological Actions and Clinical Applications of Transforming Growth Factor$ (TGF-P)", Growth Factor 8: 1-9, 1993.
Saltis et al., "Regulation and Interactions of Transforming Growth Factor-P With Cardiovascular Cells: Implications for Development and Disease", Clin. Exp. Pharmacol. Physiol. 23: 193-200, 1996.
Suzuki et al., "Discovery and in vitro and in vivo profiles of N-ethyl-N-[2-[3-(5-fluoro-2-pyridinyl)-1H-pyrazol-1-yl]ethyl]-2-(2H-1,2,3-triazol-2-yl)-benzamide as a novel class of dual orexin receptor antagonist", Bioorganic & Medicinal Chemistry, 23(6), 1260-1275, 2015.
Extended European Search Report in Application No. 17868813.1, dated Apr. 17, 2020, 7 pages.

* cited by examiner

3,4-BIPYRIDYL PYRAZOLE DERIVATIVE, AND PREPARATION METHOD THEREFOR AND MEDICAL APPLICATION THEREOF

CROSS-REFERENCE TO RELATED APPLICATIONS

This application is a National Stage Application under 35 U.S.C. § 371 and claims the benefit of International Application No. PCT/CN2017/110686, filed Nov. 13, 2017, which claims priority to CN Application No. 201610998317.8, filed Nov. 14, 2016. The disclosures of the foregoing applications are hereby incorporated by reference in their entirety.

FIELD OF THE INVENTION

The present invention belongs to the field of medicine, and relates to a novel 3,4-bipyridyl pyrazole derivative, a preparation method thereof and a pharmaceutical composition comprising the same, as well as a use thereof as a therapeutic agent, in particular as a TGF-β inhibitor, and a use thereof in the preparation of a medicament for treating, preventing or reducing cancer mediated by TGF-β overexpression.

BACKGROUND OF THE INVENTION

Transforming Growth Factor β (TGF-β) is a member of the superfamily of dimeric polypeptide growth factors that includes, for example, activins, inhibins, bone morphogenetic proteins (BMPs), growth differentiation factors (GDFs) and Müllerian-inhibiting substance (MIS).

TGF-β has three isoforms of TGF-β1, TGF-β2, and TGF-β3, which are involved in the regulation of cell proliferation and differentiation, wound healing, extracellular matrix production, and immunosuppression. See, for example, Massague, J. Ann. Rev, Cell. Biol. 6: 594-641 (1990): Roberts, A. B. Peptide Growth Factor and Their receptors, 95: 419-472 Berlin: Springer-Verlag (1990): Roberts, A. B. and Sporn M. B. Growth Factor 8: 1-9 (1993); and Alexandrow, M. G, Moses, H. L. Cancer Res. 55:1452-1457 (1995). Three isoforms of TGF-β are present in most cells along with their receptors. Each TGF-β isoform is synthesized as a precursor protein that is cleaved intracellularly into a C-terminal region (latency associated peptide, LAP) and an N-terminal part, called mature or active TGF-β. LAP typically non-covalently bonds to mature TGF-β prior to secretion from cells. The LAP-TGF-β complex cannot bind to the TGF-β receptor, and is not biologically active. TGF-β is generally released (and is active) from the complex by a variety of mechanisms including, for example, interaction with thrombospondin-1 or plasmin. TGF-β1 transduces signals through two highly conserved single transmembrane serine/threonine kinases, i.e. the type I (ALK5) and type II TGF-β receptors. Upon ligand induced oligomerization, the type II receptor hyperphosphorylates serine/threonine residues in the GS region of the ALK5, which leads to activation of the ALK5 by creating a binding site for Smad proteins. The activated ALK5 in turn phosphorylates Smad2 and Smad3 proteins at the C-terminal SSXS-motif, thereby causing their dissociation from the receptor and heteromeric complex formation with Smad4. Smad complexes translocate to the nucleus, assemble with specific DNA-binding co-factors and co-modulators to finally activate transcription of extracellular matrix components and inhibitors of matrix-degrading proteases.

The hyperactivity of the TGF-β signaling pathway is responsible for many human diseases such as excessive deposition of extracellular matrices, abnormally high levels of inflammatory responses, fibrotic disorders, and progressive cancer. The tumor cells and the stromal cells within the tumors in late stages of various cancers generally overexpress TGF-β. This leads to stimulation of angiogenesis and cell motility, suppression of the immune system, and increased interaction of tumor cells with the extracellular matrix (e.g., Hojo, M. et al., Nature 397: 530-534 (1999)). Consequently, the tumor cells become more invasive and metastasize to distant organs (e.g., Maehara, Y et al., J. Clin. Oncol. 17: 607-614 (1999); Picon, A. et al., Cancer Epidemiol. Biomarkers Prev. 7: 497-504 (1998)).

Numerous experimental animal studies demonstrate an association between glomerular expression of TGF-β and fibrosis, including the Thy-1 rat model of proliferative glomerulonephritis, anti-GBM glomerulonephritis in rabbits, and the 5/6 nephrectomy rat model of focal segmental glomerulosclerosis, as has been reviewed recently (e.g., Bitzer, M. et al., Kidney Blood Press. Res. 21: 1-12 (1998)). Neutralizing antibody to TGF-β improves glomerular histology in the Thy-1 nephritis model (e.g., Border, W. A. et al., Nature 346: 371-374 (1990)).

TGF-β and its receptors are overexpressed in injured blood vessels and in fibroproliferative vascular lesions, leading to overproduction of extracellular matrix (e.g., Saltis, J. et al., Clin. Exp. Pharmacol. Physiol. 23: 193-200 (1996); McCaffrey, T. A. et al., J Clin Invest. 96: 2667-2675 (1995)).

TGF-β2 levels are increased in most of the eyes with juvenile glaucoma in the aqueous humor of eyes and in nearly half of the eyes with primary open-angle glaucoma (POAG) (e.g., Picht, G. et al., Graefes Arch. Clin. Exp. Ophthalmol. 239: 199-207 (2001)). Both TGF-β1 and TGF-β2 isoforms are reported to increase extracellular matrix production in cultured human Tenon's capsule fibroblasts derived from patients with pseudoexfoliation glaucoma and POAG (e.g., Kottler, U. B. et al., Exp. Eye Res. 80: 121-134 (2005)).

It is therefore desirable to develop inhibitors of TGF-β family members to prevent and/or treat diseases involving such signaling pathways. Patent applications that disclose the modulators (e.g., antagonists) of the TGF-β family member receptors include WO2004111046, WO2012000595, WO2012002680, WO2013009140, WO2016106266.

The inventors hope to develop a new generation of TGF-β receptor kinase inhibitors with high efficacy and low toxicity, so as to achieve better therapeutic results and meet the needs of the market. The present invention provides a novel structure of a TGF-β receptor kinase inhibitor, and it is found that the compound of such a structure has good selective activity against ALK5. The results of toxicity assay show that the compound of such a structure has good safety. The compound exhibits excellent TGF-β receptor inhibitory activity and antitumor effect.

SUMMARY OF THE INVENTION

The object of the present invention is to provide a compound of formula (I), or a tautomer mesomer, racemate, enantiomer, diastereomer thereof, or mixture thereof, or a pharmaceutically acceptable salt thereof,

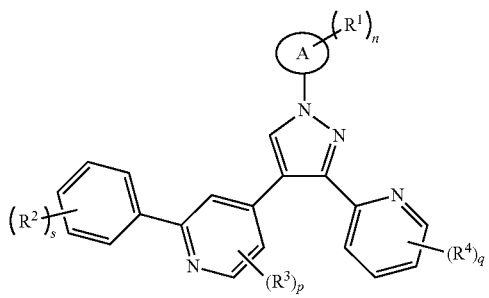

wherein:

ring A is cycloalkyl or heterocyclyl;

each $R^1$ is identical or different and each is independently selected from the group consisting of hydrogen, halogen, alkyl, alkoxy, haloalkyl, hydroxy, hydroxyalkyl, cyano, amino, nitro, —S(O)$_m$R$^5$, —C(O)OR$^5$, cycloalkyl and heterocyclyl;

each $R^2$ is identical or different and each is independently selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, —OR$^5$, —C(O)R, —S(O)$_m$R$^5$ and —C(O)NR$^6$R$^7$;

each $R^3$ is identical or different and each is independently selected from the group consisting of hydrogen, halogen, alkyl, alkoxy, haloalkyl, hydroxy, hydrohydroxyalkyl, amino, cyano and nitro:

each $R^4$ is identical or different and each is independently selected from the group consisting of hydrogen, halogen, alkyl, haloalkyl, hydroxy, hydroxyalkyl, cyano, amino, nitro, cycloalkyl, heterocyclyl, aryl and heteroaryl;

$R^5$ is selected from the group consisting of hydrogen, alkyl, amino, haloalkyl, cycloalkyl, heterocyclyl, aryl and heteroaryl;

$R^6$ and $R^7$ are each independently selected from the group consisting of hydrogen, alkyl, haloalkyl, cycloalkyl, heterocyclyl, aryl and heteroaryl;

n is 0, 1 or 2:

s is 0, 1, 2, 3, 4 or 5;

p is 0, 1, 2 or 3;

q is 0, 1, 2, 3 or 4; and m is 0, 1 or 2.

In a preferred embodiment of the present invention, the compound of formula (I) is a compound of formula (II):

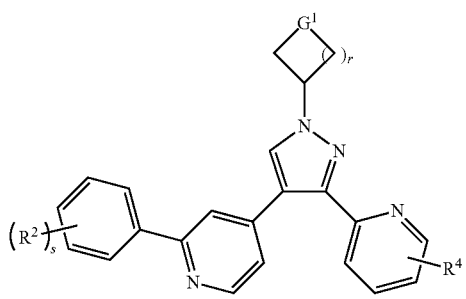

or a tautomer, mesomer, racemate, enantiomer, diastereomer thereof, or mixture thereof, or a pharmaceutically acceptable salt thereof, wherein:

$G^1$ is CH$_2$, NR$^8$ or O;

$R^8$ is selected from the group consisting of —S(O)$_m$R$^5$, —C(O)OR$^5$, hydrogen and alkyl;

$R^2$, $R^4$ and $R^5$ are as defined in formula (I);

s is 0, 1 or 2;

m is 0, 1 or 2; and r is 0, 1, 2 or 3.

In a preferred embodiment of the present invention, in the compound of formula (I), $R^2$ is selected from the group consisting of cyano, —C(O)R$^5$ and —S(O)$_m$R$^5$, $R^5$ is hydroxy or alkyl, preferably, $R^2$ is cyano and methanesulfonyl, and s is 1.

In a preferred embodiment of the present invention, in the compound of formula (I), $R^4$ is alkyl.

The compound of the present invention includes all conformational isomers thereof, e.g., cis-isomers and trans-isomers: and all optical isomers and stereoisomers and mixtures thereof. The compound of the present invention has asymmetric centers, and therefore there are different enantiomeric and diastereomeric isomers. The present invention relates to the use of the compound of the present invention, and the pharmaceutical composition applying and comprising the same, and the therapeutic method thereof. The present invention relates to the use of all such tautomers and mixtures thereof.

Typical compounds of the present invention include, but are not limited to.

| Example No. | Structure and name of the compound |
|---|---|
| 1 | ![structure 1]<br>1<br>4-(1-cyclobutyl-3-(6-methylpyridin-2-yl)-1H-pyrazol-4-yl)-2-(4-(methylsulfonyl)phenyl)pyridine |
| 2 | ![structure 2]<br>2<br>4-(1-cyclopropyl-3-(6-methylpyridin-2-yl)-1H-pyrazol-4-yl)-2-(4-(methylsulfonyl)phenyl)pyridine |

-continued

| Example No. | Structure and name of the compound |
|---|---|
| 3 | 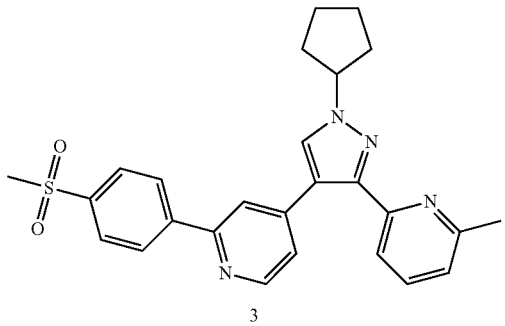<br>3<br>4-(1-cyclopentyl-3-(6-methylpyridin-2-yl)-1H-pyrazol-4-yl)-2-(4-(methylsulfonyl)phenyl)pyridine |
| 4 | 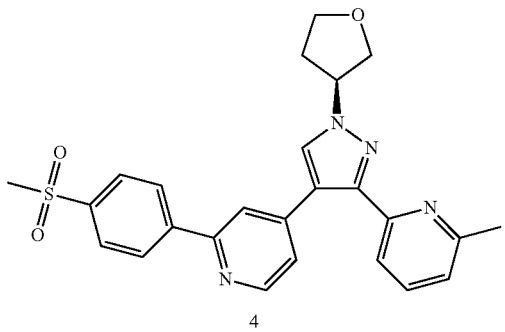<br>4<br>(S)-4-(3-(6-methylpyridin-2-yl)-1-(tetrahydrofuran-3-yl)-1H-pyrazol-4-yl)-2-(4-(methylsulfonyl)phenyl)pyridine |
| 5 | 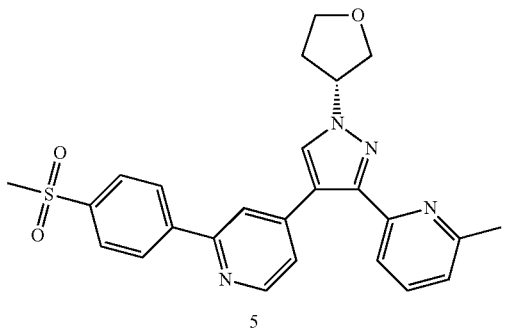<br>5<br>(R)-4-(3-(6-methylpyridin-2-yl)-1-(tetrahydrofuran-3-yl)-1H-pyrazol-4-yl)-2-(4-(methylsulfonyl)phenyl)pyridine |
| 6 | 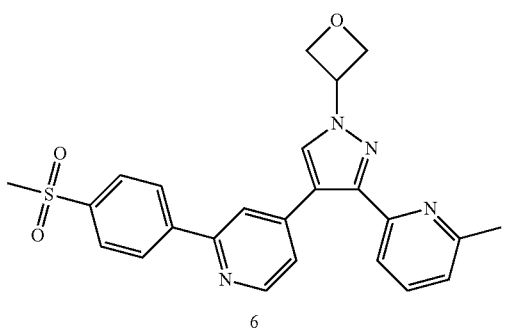<br>6<br>4-(3-(6-methylpyridin-2-yl)-1-(oxetan-3-yl)-1H-pyrazol-4-yl)-2-(4-(methylsulfonyl)phenyl)pyridine |

-continued

| Example No. | Structure and name of the compound |
|---|---|
| 7 | 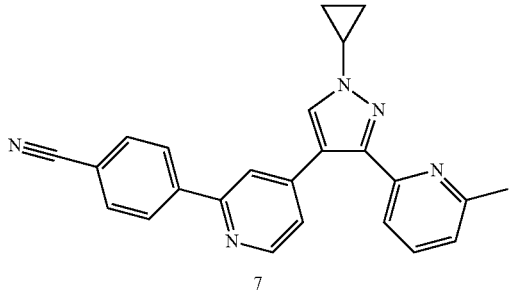 [SMILES: Cc1cccc(-c2nn(C3CC3)cc2-c2ccnc(-c3ccc(C#N)cc3)c2)n1]<br>7<br>4-(4-(1-cyclopropyl-3-(6-methylpyridin-2-yl)-1H-pyrazol-4-yl)pyridin-2-yl)benzonitrile 7 |
| 8 | 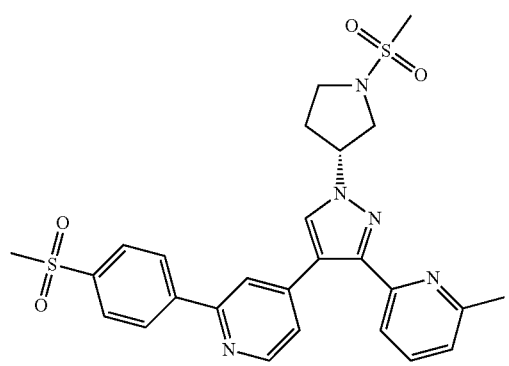<br>8<br>(R)-4-(3-(6-methylpyridin-2-yl)-1-(1-methylsulfonyl)pyrrolidin-3-yl)-1H-pyrazol-4-yl)-2-(4-(methylsulfonyl)phenyl)pyridine 8 |
| 8d | 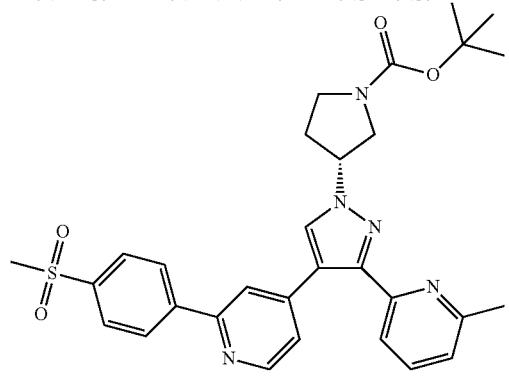<br>8d<br>tert-butyl (R)-3-(3-(6-methylpyridin-2-yl)-4-(2-(4-(methylsulfonyl)phenyl)pyridin-4-yl)-1H-pyrazol-1-yl)pyrrolidine-1-carboxylate 8d |
|  | 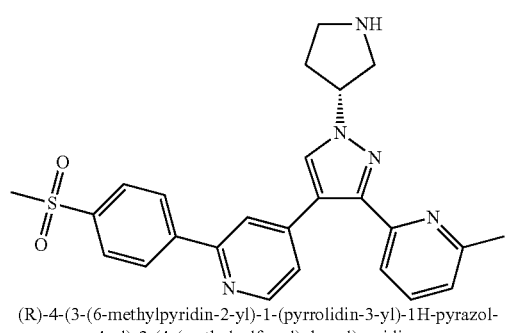<br>(R)-4-(3-(6-methylpyridin-2-yl)-1-(pyrrolidin-3-yl)-1H-pyrazol-4-yl)-2-(4-(methylsulfonyl)phenyl)pyridine | or a tautomer, mesomer, racemate, enantiomer, diastereomer thereof, or mixture thereof, or a pharmaceutically acceptable salt thereof.

The present invention also relates to a compound of formula (I-A) which is an intermediate for synthesizing the compound of formula (I):

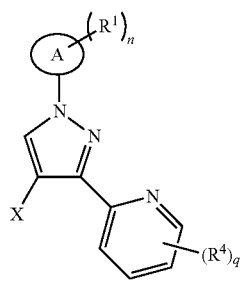

(I-A)

or a tautomer, mesomer, racemate, enantiomer, diastereomer thereof, or mixture thereof, or a pharmaceutically acceptable salt thereof.

wherein:

X is halogen, and preferably bromine:

ring A, $R^1$, $R^4$, n and q are as defined in formula (I).

The compounds of formula (I-A) include, but are not limited to:

| Example No. | Structure and name |
|---|---|
| 1h | 1h<br>2-(4-bromo-1-cyclobutyl-1H-pyrazol-3-yl)-6-methylpyridine 1h |
| 2c | 2c<br>2-(4-bromo-1-cyclopropyl-1H-pyrazol-3-yl)-6-methylpyridine 2c |
| 3d | 3d<br>2-(4-bromo-1-cyclopentyl-1H-pyrazol-3-yl)-6-methylpyridine 3d |
| 4c | 4c<br>(S)-2-(4-bromo-1-(tetrahydrofuran-3-yl)-1H-pyrazol-3-yl)-6-methylpyridine 4c |
| 5c | 5c<br>(R)-2-(4-bromo-1-(tetrahydrofuran-3-yl)-1H-pyrazol-3-yl)-6-methylpyridine 5c |
| 6c | 6c<br>2-(4-bromo-1-(oxetan-3-yl)-1H-pyrazol-3-yl)-6-methylpyridine 6c |

In another aspect, the present invention relates to a method for preparing the compound of formula (I), comprising a step of:

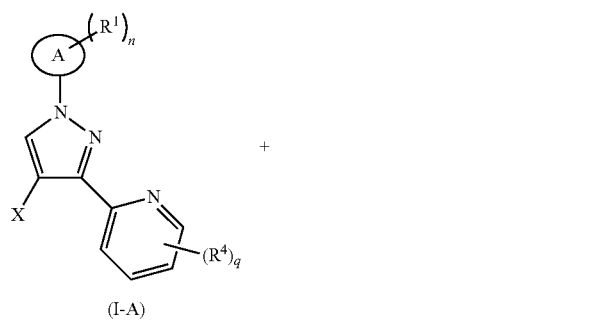

(I-A)

+

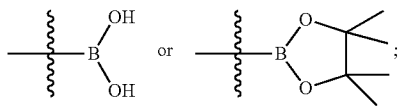

(I-B)

→

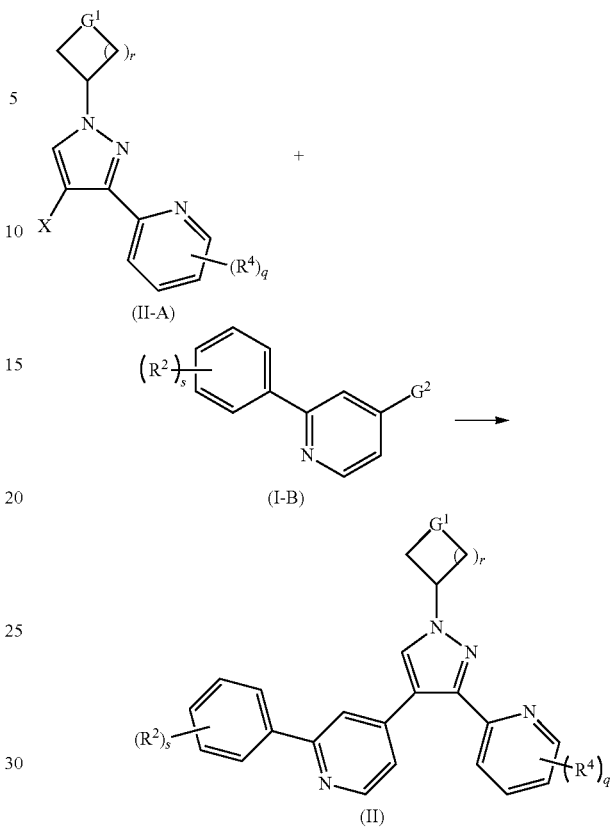

subjecting a compound of formula (I-A) and a compound of formula (I-B) to a Suzuki reaction under an alkaline condition in the presence of a catalyst to obtain the compound of formula (I), wherein:

G² is

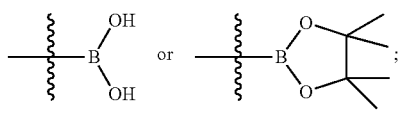

X is halogen, and preferably bromine;

ring A, R¹~R⁴, n, s, p and q are as defined in formula (I).

In another aspect, the present invention relates to a method for preparing the compound of formula (II), comprising a step of:

subjecting a compound of formula (II-A) and a compound of formula (I-B) to a Suzuki reaction under an alkaline condition in the presence of a catalyst to obtain the compound of formula (II), wherein:

G² is

X is halogen, and preferably bromine:

G¹, R², R⁴, r, s and q are as defined in formula (I).

In another aspect, the present invention relates to a pharmaceutical composition comprising a therapeutically effective amount of the compound of formula (I), or a tautomer, mesomer, racemate, enantiomer, diastereomer thereof, or mixture thereof, or a pharmaceutically acceptable salt thereof, and one or more pharmaceutically acceptable carriers, diluents or excipients. The present invention also relates to a method for preparing the aforementioned composition, comprising a step of mixing the compound of formula (I), or a tautomer, mesomer, racemate, enantiomer, diastereomer thereof, or mixture thereof, or a pharmaceutically acceptable salt thereof, with one or more pharmaceutically acceptable carriers, diluents or excipients.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same, in the preparation of a medicament for inhibiting the TGF-β and/or activin (particularly human TGF-β and/or activin) signaling pathway.

The present invention further relates to a use of the compound of formula (I), or a tautomer mesomer, racemate, enantiomer, diastereomer thereof, or mixture thereof, or a pharmaceutically acceptable salt thereof, or the pharmaceutical composition comprising the same, in the preparation of a medicament for treating, preventing or reducing the metastasis of tumor cells, particularly human tumor cells.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same, in the preparation of a medicament for treating, preventing or reducing cancer mediated by TGF-β overexpression, particularly in the preparation of a medicament for treating, preventing, or reducing cancer mediated by TGF-β overexpression by inhibiting the human TGF-β signaling pathway.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same, in the preparation of a medicament for treating, preventing or reducing a disease (particularly in human) selected from the group consisting of vascular injury, glomerulonephritis, diabetic nephropathy, lupus nephritis, hypertension-induced nephropathy, renal interstitial fibrosis, renal fibrosis resulting from complications of drug exposure, HIV-associated nephropathy, transplant nephropathy, liver fibrosis due to all etiologies, hepatic dysfunction attributable to infections, alcohol-induced hepatitis, cystic fibrosis, interstitial lung disease, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomnopathy, myocarditis, intimal thickening, vascular stenosis, hypertension-induced vascular remodeling, pulmonary arterial hypertension, coronary restenosis, peripheral restenosis, carotid restenosis, stent-induced restenosis, atherosclerosis, ocular scarring, corneal scarring, proliferative vitreoretinopathy, glaucoma, high intraocular pressure, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Peyronie's disease, Dupuytren's contracture, Alzheimer's disease, Raynaud's syndrome, radiation-induced fibrosis, thrombosis, tumor metastasis growth, multiple myeloma, melanoma, glioma, glioblastomas, leukemia, sarcomas, leiomyomas, mesothelioma, breast cancer, cervical cancer, lung cancer, stomach cancer rectal cancer, colon cancer, pancreatic cancer, brain cancer, skin cancer, oral cancer prostate cancer, bone cancer, kidney cancer, ovarian cancer, bladder cancer and liver cancer.

The present invention further relates to a method for treating, preventing or reducing the metastasis of human tumor cells, comprising administering to a patient in need thereof a therapeutically effective amount of the compound of formula (I), or a tautomer mesomer, racemate, enantiomer, diastereomer thereof, or mixture thereof, or a pharmaceutically acceptable salt thereof, or the pharmaceutical composition comprising the same.

The present invention further relates to a method for treating, preventing or reducing cancer mediated by TGF-β overexpression, in particular a method for treating, preventing or reducing cancer mediated by TGF-β overexpression by inhibiting the TGF-β signaling pathway, comprising administering to a patient in need thereof a therapeutically effective amount of the compound of formula (I), or a tautomer, mesomer, racemate, enantiomer, diastereomer thereof or mixture thereof or a pharmaceutically acceptable salt thereof, or the pharmaceutical composition comprising the sane.

The present invention further relates to a method for treating, preventing or reducing a disease (particularly in human) selected from the group consisting of vascular injury, glomerulonephritis, diabetic nephropathy, lupus nephritis, hypertension-induced nephropathy, renal interstitial fibrosis, renal fibrosis resulting from complications of drug exposure, HIV-associated nephropathy, transplant nephropathy, liver fibrosis due to all etiologies, hepatic dysfunction attributable to infections, alcohol-induced hepatitis, cystic fibrosis, interstitial lung disease, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, intimal thickening, vascular stenosis, hypertension-induced vascular remodeling, pulmonary arterial hypertension, coronary restenosis, peripheral restenosis, carotid restenosis, stent-induced restenosis, atherosclerosis, ocular scarring, corneal scarring, proliferative vitreoretinopathy, glaucoma, high intraocular pressure, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Peyronie's disease, Dupuytren's contracture, Alzheimer's disease, Raynaud's syndrome, radiation-induced fibrosis, thrombosis, tumor metastasis growth, multiple myeloma, melanoma, glioma, glioblastomas, leukemia, sarcomas, leiomyomas, mesothelioma, breast cancer, cervical cancer, lung cancer, stomach cancer, rectal cancer, colon cancer, pancreatic cancer, brain cancer, skin cancer, oral cancer, prostate cancer, bone cancer, kidney cancer, ovarian cancer, bladder cancer and liver cancer, comprising administering to a patient in need thereof a therapeutically effective amount of the compound of formula (I), or a tautomer, mesomer, racemate, enantiomer, diastereomer thereof, or mixture thereof, or a pharmaceutically acceptable salt thereof, or the pharmaceutical composition comprising the same.

The present invention further relates to the compound of formula (I), or a tautomer, mesomer, racemate, enantiomer, diastereomer thereof or mixture thereof or a pharmaceutically acceptable salt thereof, or the pharmaceutical composition comprising the same, for use as a medicament.

The present invention further relates to the compound of formula (I), or a tautomer, mesomer, racemate, enantiomer diastereomer thereof, or mixture thereof, or a pharmaceutically acceptable salt thereof, or the pharmaceutical composition comprising the same, for use as a TGF-β receptor kinase inhibitor.

The present invention further relates to the compound of formula (I), or a tautomer, mesomer, racemate, enantiomer, diastereomer thereof, or mixture thereof, or a pharmaceutically acceptable salt thereof, or the pharmaceutical composition comprising the same, for use in treating, preventing or reducing the metastasis of tumor cells, particularly human tumor cells.

The present invention further relates to the compound of formula (I), or a tautomer, mesomer, racemate, enantiomer diastereomer thereof, or mixture thereof, or a pharmaceutically acceptable salt thereof, or the pharmaceutical composition comprising the same, for use in treating, preventing or reducing cancer mediated by TGF-β overexpression, in particular in treating, preventing or reducing cancer mediated by TGF-β overexpression by inhibiting the TGF-β signaling pathway.

The present invention further relates to the compound of formula (I), or a tautomer, mesomer, racemate, enantiomer, diastereomer thereof, or mixture thereof, or a pharmaceutically acceptable salt thereof, or the pharmaceutical composition comprising the same, for use in treating, preventing or reducing a disease (particularly in human) selected from the group consisting of vascular injury, glomerulonephritis, diabetic nephropathy, lupus nephritis, hypertension-induced nephropathy, renal interstitial fibrosis, renal fibrosis resulting from complications of drug exposure, HIV-associated nephropathy, transplant nephropathy, liver fibrosis due to all etiologies, hepatic dysfunction attributable to infections, alcohol-induced hepatitis, cystic fibrosis, interstitial lung disease, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, intimal thickening, vascular stenosis, hypertension-induced vascular remodeling, pulmonary arterial hypertension, coronary restenosis, peripheral restenosis, carotid restenosis, stent-induced restenosis, atherosclerosis, ocular scarring, corneal scarring, proliferative vitreoretinopathy, glaucoma, high intraocular pressure, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Peyronie's disease, Dupuytren® s contracture, Alzheimer's disease, Raynaud's syndrome, radiation-induced fibrosis, thrombosis, tumor metastasis growth, multiple myeloma, melanoma, glioma, glioblastomas, leukemia, sarcomas, leiomyomas, mesothelioma, breast cancer, cervical cancer, lung cancer, stomach cancer, rectal cancer, colon cancer, pancreatic cancer, brain cancer, skin cancer, oral cancer, prostate cancer, bone cancer, kidney cancer, ovarian cancer, bladder cancer and liver cancer.

Pharmaceutical compositions containing the active ingredient can be in a form suitable for oral administration, for example, a tablet, troche, lozenge, aqueous or oily suspension, dispersible powder or granule, emulsion, hard or soft capsule, or syrup or elixir. Oral compositions can be prepared according to any known method in the art for the preparation of pharmaceutical composition. Such composition can contain one or more ingredients selected from the group consisting of sweeteners, flavoring agents, colorants and preservatives, in order to provide a pleasing and palatable pharmaceutical preparation. Tablets contain the active ingredient in admixture with nontoxic pharmaceutically acceptable excipients suitable for the manufacture of tablets.

An aqueous suspension contains the active ingredient in admixture with excipients suitable for the manufacture of an aqueous suspension. Such an excipient is a suspending agent.

An oil suspension can be formulated by suspending the active ingredient in a vegetable oil. The oil suspension can contain a thickener. The aforementioned sweeteners and flavoring agents can be added to provide a palatable formulation. These compositions can be preserved by adding an antioxidant.

The active ingredient in admixture with the dispersants or wetting agents, suspending agent or one or more preservatives can be prepared as a dispersible powder or granule suitable for the preparation of an aqueous suspension by adding water. Suitable dispersants or wetting agents and suspending agents are exemplified by those already mentioned above. Additional excipients, such as sweeteners, flavoring agents and colorants, can also be added. These compositions are preserved by adding an antioxidant.

The pharmaceutical composition of the present invention can also be in the form of an oil-in-water emulsion. The oil phase can be a vegetable oil. Suitable emulsifying agents can be naturally occurring phosphatides. The emulsion can also contain sweeteners, flavoring agents, preservatives and antioxidants. Such formulations can also contain demulcents, preservatives, colorants, and antioxidants.

The pharmaceutical composition of the present invention can be in the form of a sterile injectable aqueous solution. The sterile injectable formulation can be a sterile injectable oil-in-water microemulsion in which the active ingredient is dissolved in the oil phase.

The pharmaceutical composition of the present invention can be in the form of a sterile injectable aqueous or oily suspension for intramuscular and subcutaneous administration. Such a suspension can be formulated with suitable dispersants or wetting agents and suspending agents as described above according to known techniques. The sterile injectable formulation can also be a sterile injectable solution or suspension prepared in a nontoxic parenterally acceptable diluent or solvent. Moreover, sterile fixed oils can easily be used as a solvent or suspending medium.

The compound of the present invention can be administered in the form of a suppository for rectal administration. These pharmaceutical compositions can be prepared by mixing the drug with a suitable non-irritating excipient that is solid at ordinary temperatures, but liquid in the rectum, thereby melting in the rectum to release the drug.

It is well known to those skilled in the art that the dosage of a drug depends on a variety of factors including but not limited to, the following factors: activity of a specific compound, age of the patient, weight of the patient, general health of the patient, behavior of the patient, diet of the patient, administration time, administration route, excretion rate, drug combination and the like. In addition, the optimal treatment, such as treatment mode, daily dose of the compound of formula (I) or the type of pharmaceutically acceptable salt thereof can be verified by traditional therapeutic regimens.

PREFERRED EMBODIMENT

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 12 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-dimethylpentyl, n-decyl, 3,3-diethylhexyl, 2,2-diethylhexyl, and various branched isomers thereof. More preferably, an alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, I-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently optionally selected from the group consisting of alkyl, alkenyl, alkynyl, alkoxy alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, —OR$^5$, —C(O)R$^5$, —S(O)$_m$R$^5$ and —C(O)NR$^6$R$^7$.

The term "cycloalkyl" refers to a saturated or partially unsaturated monocyclic or polycyclic hydrocarbon group having 3 to 20 carbon atoms, preferably 3 to 12 carbon atoms, more preferably 3 to 10 carbon atoms, and most preferably 3 to 6 carbon atoms, for example 3, 4, 5 or 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like, preferably cyclopropyl, cyclobutyl, cyclopentyl and cyclohexyl. Polycyclic cycloalkyl includes a cycloalkyl having a spiro ring, fused ring or bridged ring.

The term "spiro cycloalkyl" refers to a 5 to 20 membered polycyclic group with monocyclic rings connected through one shared carbon atom (called a spiro atom), wherein the rings can contain one or more double bonds, but none of the rings has a completely conjugated i-electron system. The spiro cycloallyl is preferably 6 to 14 membered spiro cycloalkyl, and more preferably 7 to 10 membered spiro cycloalkyl. According to the number of the spiro atoms shared between the rings, the spiro cycloalkyl can be divided into mono-spiro cycloalkyl, di-spiro cycloalkyl, or poly-spiro cycloalkyl, and the spiro cycloalkyl is preferably a mono-spiro cycloalkyl or di-spiro cycloalkyl, and more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

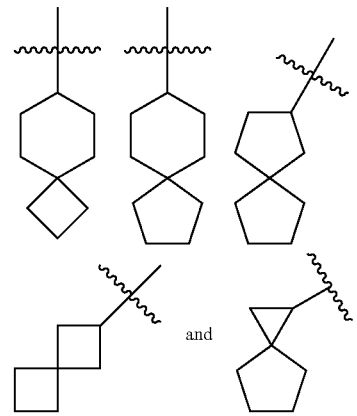

The term "fused cycloalkyl" refers to a 5 to 20 membered all-carbon polycyclic group, wherein each ring in the system shares an adjacent pair of carbon atoms with another ring, wherein one or more rings can contain one or more double bonds, but none of the rings has a completely conjugated n-electron system. The fused cycloalkyl is preferably 6 to 14 membered fused cycloalkyl, and more preferably 7 to 10 membered fused cycloalkyl. According to the number of membered rings, the fused cycloalkyl can be divided into bicyclic, tricyclic, tetracyclic or polycyclic fused cycloalkyl, and the fused cycloalkyl is preferably bicyclic or tricyclic fused cycloalkyl, and more preferably 5-membered/5-membered, or 5-membered/6-membered bicyclic fused cycloalkyl. Non-limiting examples of fused cycloalkyl include:

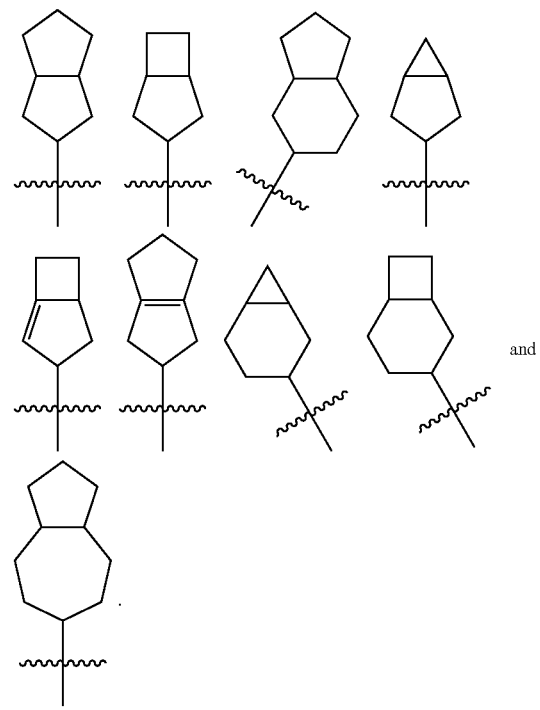

The term "bridged cycloalkyl" refers to a 5 to 20 membered all-carbon polycyclic group, wherein every two rings in the system share two disconnected carbon atoms, wherein the rings can have one or more double bonds, but none of the rings has a completely conjugated π-electron system. The bridged cycloalkyl is preferably 6 to 14 membered bridged cycloalkyl, and more preferably 7 to 10 membered bridged cycloalkyl. According to the number of membered rings, the bridged cycloalkyl can be divided into bicyclic, tricyclic, tetracyclic or polycyclic bridged cycloalkyl, and the bridged cycloalkyl is preferably bicyclic, tricyclic or tetracyclic bridged cycloalkyl, and more preferably bicyclic or tricyclic bridged cycloalkyl. Non-limiting examples of bridged cycloalkyls include:

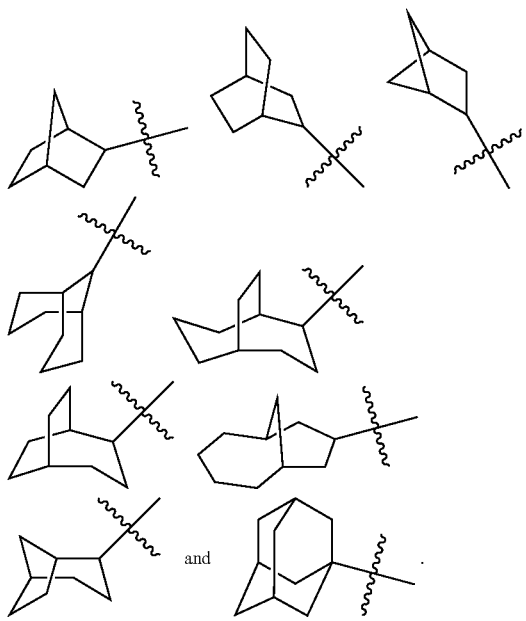

and

The ring of cycloalkyl can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more group(s) independently optionally selected from the group consisting of alkyl, alkenyl, alkynyl, alkoxy, alkyl, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, —$OR^5$, —$C(O)R^5$, —$S(O)_mR^5$ and —$C(O)NR^6R^7$.

The term "heterocyclyl" refers to a 3 to 20 membered saturated or partially unsaturated monocyclic or polycyclic hydrocarbon group, wherein one or more ring atoms are heteroatoms selected from the group consisting of N, O, and $S(O)_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms, for example 1, 2, 3 or 4 atoms are heteroatoms, more preferably the heterocyclyl has 3 to 10 ring atoms, and most preferably the heterocyclyl has 3 to 6 ring atoms, for example 3, 4, 5 or 6 ring atoms. Non-limiting examples of monocyclic heterocyclyl include oxetanyl, tetrahydrofuranyl, tetrahydropyranyl, pyrrolyl, piperidinyl, piperazinyl, morpholinyl, thiomorpholinyl, homopiperazinyl and the like, and preferably oxetanyl and tetrahydrofuranyl. Polycyclic heterocyclyl includes a heterocyclyl having a spiro ring, fused ring or bridged ring.

The term "spiro heterocyclyl" refers to a 5 to 20 membered polycyclic heterocyclyl with monocyclic rings connected through one shared atom (called a spiro atom), wherein one or more ring atoms are heteroatoms selected from the group consisting of N, O, and $S(O)_m$ (wherein m is an integer of 0 to 2), with the remaining ring atoms being carbon atoms. The rings can contain one or more double bonds, but none of the rings has a completely conjugated π-electron system. The spiro heterocyclyl is preferably 6 to 14 membered spiro heterocyclyl, and more preferably 7 to 10 membered spiro heterocyclyl. According to the number of the spiro atoms shared between the rings, the spiro heterocyclyl can be divided into mono-spiro heterocyclyl, di-spiro heterocyclyl, or poly-spiro heterocyclyl, and the spiro heterocyclyl is preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Non-limiting examples of spiro heterocyclyls include:

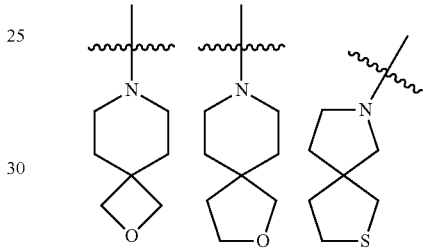

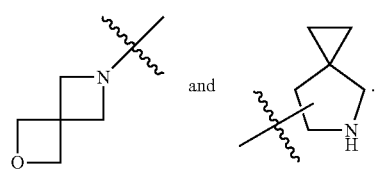

The term "fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated π-electron system, and wherein one or more ring atoms are heteroatoms selected from the group consisting of N, O, and $S(O)_m$ (wherein m is an integer of 0 to 2), with the remaining ring atoms being carbon atoms. The fused heterocyclyl is preferably 6 to 14 membered fused heterocyclyl, and more preferably 7 to 10 membered fused heterocyclyl. According to the number of membered rings, the fused heterocyclyl can be divided into bicyclic, tricyclic, tetracyclic or polycyclic fused heterocyclyl, and the fused heterocyclyl is preferably bicyclic or tricyclic fused heterocyclyl, and more preferably 5-membered/5-membered, or 5-membered/6-membered bicyclic fused heterocyclyl. Non-limiting examples of fused heterocyclyl include:

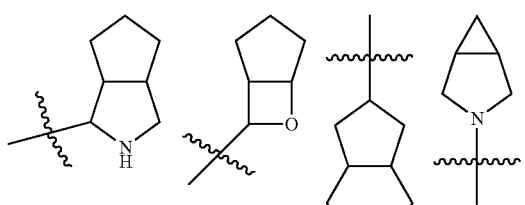

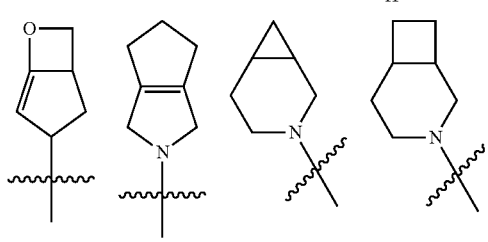

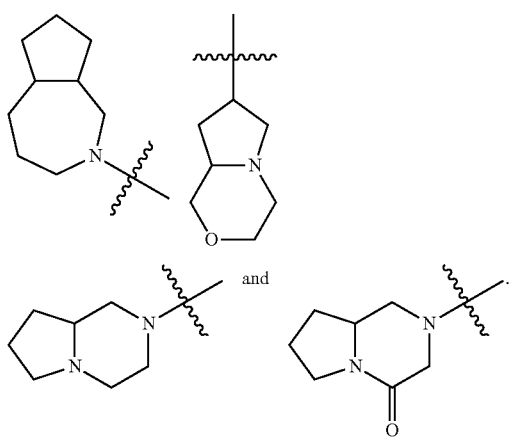

The term "bridged heterocyclyl" refers to a 5 to 14 membered polycyclic heterocyclyl group, wherein every two rings in the system share two disconnected atoms, wherein the rings can have one or more double bonds, but none of the rings has a completely conjugated π-electron system, and wherein one or more ring atoms are heteroatoms selected from the group consisting of N, O, and $S(O)_m$ (wherein m is an integer of 0 to 2), with the remaining ring atoms being carbon atoms. The bridged heterocyclyl is preferably 6 to 14 membered bridged heterocyclyl, and more preferably 7 to 10 membered bridged heterocyclyl. According to the number of membered rings, the bridged heterocyclyl can be divided into bicyclic, tricyclic, tetracyclic or polycyclic bridged heterocyclyl, and the bridged heterocyclyl is preferably bicyclic, tricyclic or tetracyclic bridged heterocyclyl, and more preferably bicyclic or tricyclic bridged heterocyclyl. Non-limiting examples of bridged heterocyclyl include:

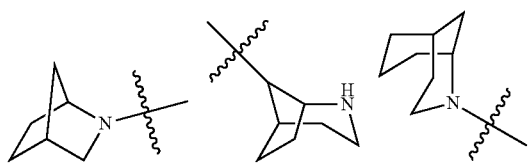

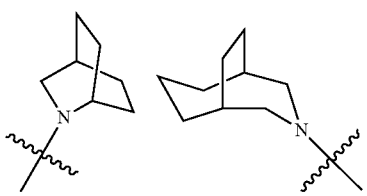

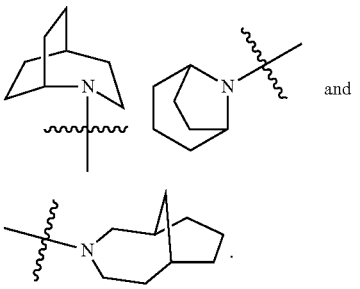 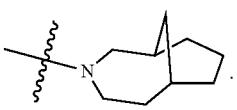

The ring of heterocyclyl can be fused to the ring of aryl, heteroaryl or cycloalkyl, wherein the ring bound to the parent structure is heterocyclyl. Non-limiting examples include:

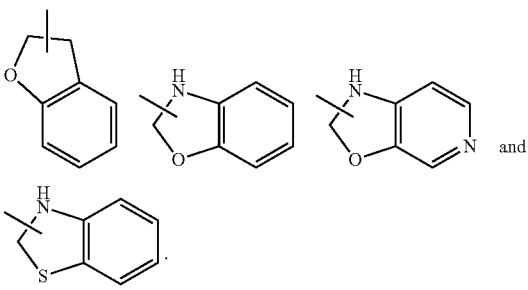

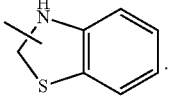

The heterocyclyl can be optionally substituted or unsubstituted. When substituted, the substituent group(s) is preferably one or more group(s) independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, —$OR^5$, —$C(O)R^3$, —$S(O)_mR^5$ and —$C(O)NR^6R^7$.

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably 6 to 10 membered aryl, for example, phenyl and naphthyl. The ring of aryl can be fused to the ring of heteroaryl, heterocyclyl or cycloalkyl, wherein the ring bound to the parent structure is aryl ring. Non-limiting examples include:

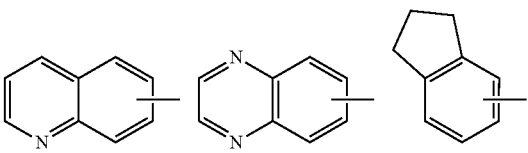

-continued

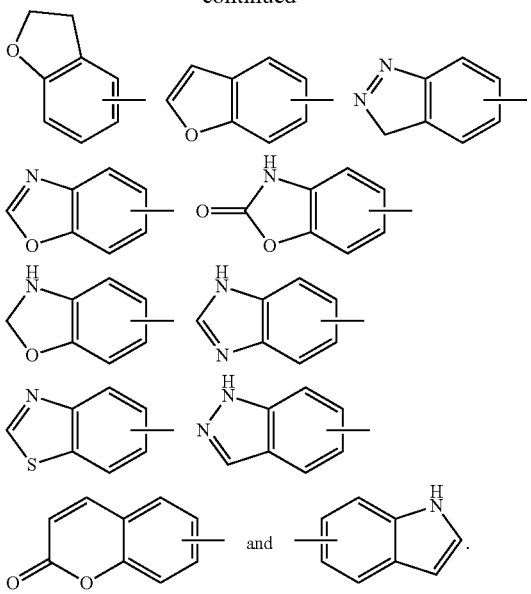

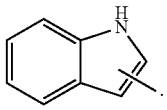

The aryl can be substituted or unsubstituted. When substituted, the substituent group(s) is preferably one or more group(s) independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, —OR$^5$, —C(O)R$^5$, —S(O)$_m$R$^5$ and —C(O)NR$^6$R$^7$.

The term "heteroaryl" refers to a 5 to 14 membered heteroaromatic system having 1 to 4 heteroatoms selected from the group consisting of O, S and N. The heteroaryl is preferably 5 to 10 membered heteroaryl, more preferably 5 or 6 membered heteroaryl, for example, furanyl, thienyl, pyridyl, pyrrolyl, N-alkylpyrrolyl, pyrimidinyl, pyrazinyl, imidazolyl, pyrazolyl, tetrazolyl, and the like. The ring of heteroaryl can be fused to the ring of aryl, heterocyclyl or cycloalkyl, wherein the ring bound to the parent structure is heteroaryl ring. Non-limiting examples include:

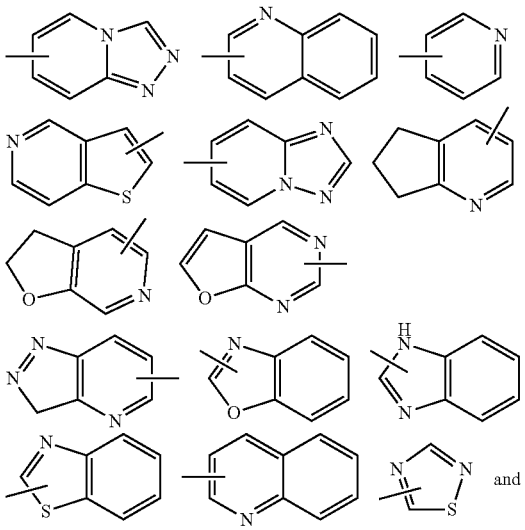

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, —OR$^5$, —C(O) R$^5$, —S(O)$_m$R$^5$ and —C(O)NR$^6$R$^7$.

The term "alkoxy" refers to an —O—(alkyl) or an —O—(unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, amino, nitro, cyano, cycloalkyl, heterocyclyl, aryl, heteroaryl, cycloalkoxy heteroalkoxy, cycloalkylthio, heterocyclylthio, —OR$^5$, —C(O)R$^5$, —S(O)$_m$R$^5$ and —C(O)NR$^6$R$^7$.

The term "hydroxyalkyl" refers to an alkyl group substituted by hydroxy(s), wherein the alkyl is as defined above.

The term "haloalkyl" refers to an alkyl group substituted by one or more halogens, wherein alkyl is as defined above.

The term "hydroxy" refers to an —OH group.

The term "halogen" refers to fluorine, chlorine, bromine or iodine.

The term "amino" refers to a —NH$_2$ group.

The term "cyano" refers to a —CN group.

The term "nitro" refers to a —NO$_2$ group.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) may be unstable.

A "pharmaceutical composition" refers to a mixture comprising one or more of the compounds according to the present invention or physiologically/pharmaceutically acceptable salts or prodrugs thereof with other chemical components, and other components such as physiologically/pharmaceutically acceptable carriers and excipients.

The purpose of the pharmaceutical composition is to facilitate administration of a compound to an organism, which is conducive to the absorption of the active ingredient so as to show biological activity.

A "pharmaceutically acceptable salt" refers to a salt of the compound of the present invention, which is safe and effective in mammals and has the desired biological activity.

m and $R^5$ to $R^7$ are as defined in the formula (I).

DETAILED DESCRIPTION OF THE INVENTION

Figure 1:
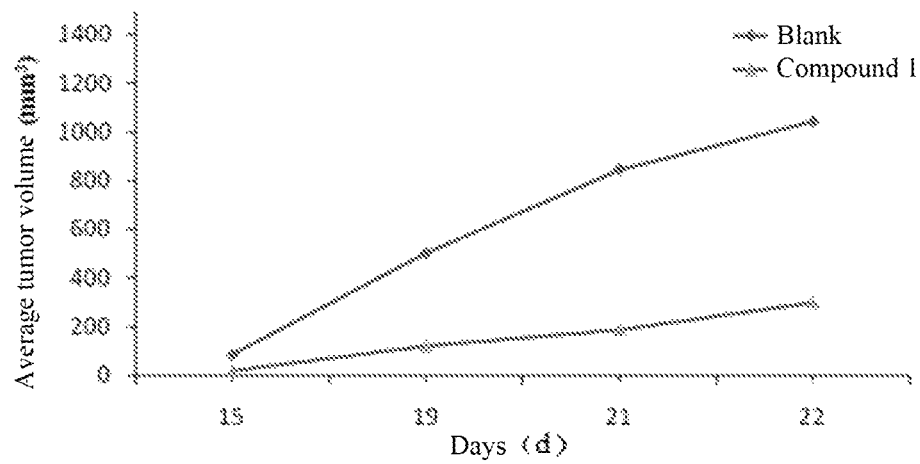
FIG. 1 shows the effect of compound 1 on the xenograft volume of B16-F1 tumor-bearing C57 mice.

Synthesis Method of the Compound of the Present Invention

In order to achieve the objective of the present invention, the present invention applies the following technical solutions:

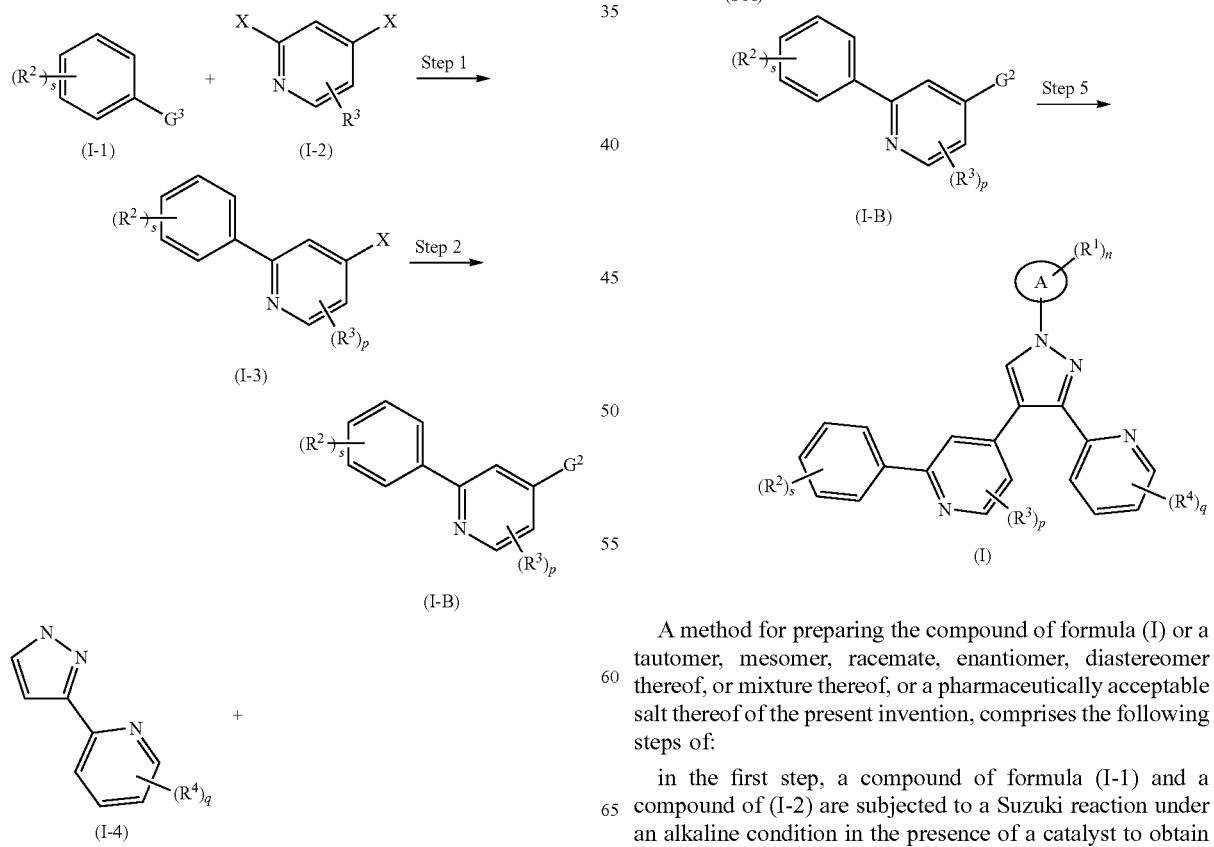

A method for preparing the compound of formula (I) or a tautomer, mesomer, racemate, enantiomer, diastereomer thereof, or mixture thereof, or a pharmaceutically acceptable salt thereof of the present invention, comprises the following steps of:

in the first step, a compound of formula (I-1) and a compound of (I-2) are subjected to a Suzuki reaction under an alkaline condition in the presence of a catalyst to obtain a compound of formula (I-3);

in the second step, the compound of formula (I-3) is reacted with bis(pinacolato)diboron under an alkaline condition in the presence of a catalyst to obtain a compound of formula (I-B);

in the third step, a compound of formula (I-4) is reacted with a compound of formula (I-5) under an alkaline condition to obtain a compound of formula (I-6);

in the fourth step, the compound of formula (I-6) is reacted with a halogenating agent to obtain a compound of formula (I-A);

in the fifth step, the compound of formula (I-A) and the compound of formula (I-B) are subjected to a Suzuki reaction under an alkaline condition in the presence of a catalyst to obtain the compound of formula (I).

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, sodium tert-butoxide and potassium tert-butoxide. The inorganic bases include, but are not limited to, sodium hydride, potassium phosphate, sodium carbonate, potassium carbonate, potassium acetate, cesium carbonate, sodium hydroxide and lithium hydroxide.

The catalyst includes, but is not limited to, palladium on carbon, Raney nickel, tetrakis(triphenylphosphine)palladium, palladium dichloride, palladium acetate, [1,1'-bis(diphenylphosphino)ferrocene]dichloropalladium, 1,1'-bis(diphenylphosphino)ferrocene palladium dichloride or tris(dibenzylideneacetone)dipalladium, and preferably [1,1-bis(diphenylphosphino)ferrocene]dichloropalladium or tetrakis(triphenylphosphine)palladium.

The halogenating agent includes, but is not limited to, liquid bromine, hydrogen bromide, N-bromosuccinimide (NBS), $PBr_3$, $POBr_3$, pyridine hydrobromide perbromide (PHP), 2A,4,4,6-tetrabromo-2,5-cyclohexadienone (TBCO), diethyl bromomalonate, tetrabutylammonium bromide, N-chlorosuccinimide, $PCl_3$ and $POCl_3$.

The above reactions are preferably carried out in a solvent. The solvent used includes, but not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof Wherein:

$G^2$ and $G^3$ are each independently selected from the group consisting of

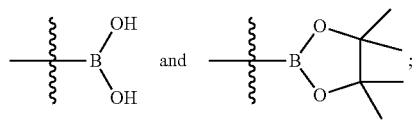

X is halogen, and preferably bromine:

ring A, $R^1$~$R^4$, n, s, p and q are as defined in formula (I).

Scheme II
A method for preparing the compound of formula (II) or a tautomer, mesomer, racemate, enantiomer, diastereomer thereof, or mixture thereof, or a pharmaceutically acceptable salt thereof of the present invention, comprises the following steps of:

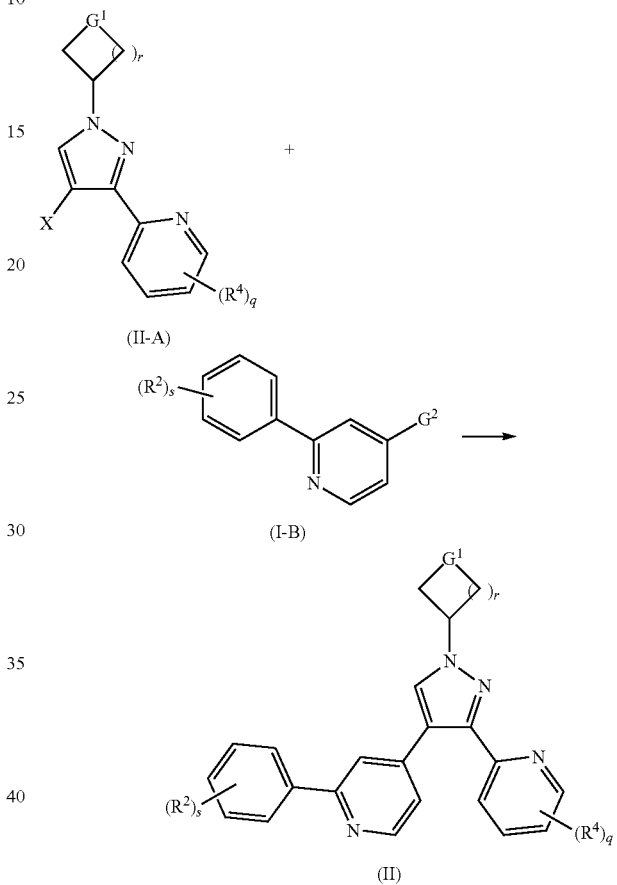

A method for preparing the compound of formula (II) or a tautomer, mesomer, racemate, enantiomer, diastereomer thereof, or mixture thereof, or a pharmaceutically acceptable salt thereof of the present invention, comprises the following steps of:

subjecting a compound of formula (II-A) and a compound of formula (I-B) to a Suzuki reaction under an alkaline condition in the presence of a catalyst to obtain the compound of formula (II).

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, sodium tert-butoxide and potassium tert-butoxide. The inorganic bases include, but are not limited to, sodium hydride, potassium phosphate, sodium carbonate, potassium carbonate, potassium acetate, cesium carbonate, sodium hydroxide and lithium hydroxide.

The catalyst includes, but is not limited to, palladium on carbon, Raney nickel, tetrakis(triphenylphosphine)palladium, palladium dichloride, palladium acetate, [1,1'-bis(diphenylphosphino)ferrocene]dichloropalladium, 1,1'-bis(diphenylphosphino)ferrocene palladium dichloride or tris(dibenzylideneacetone)dipalladium, and preferably [1,1'-bis(diphenylphosphino)ferrocene]dichloropalladium or tetrakis(triphenylphosphine)palladium.

The above reactions are preferably carried out in a solvent. The solvent used includes, but not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof Wherein:

$G^2$ is selected from the group consisting of

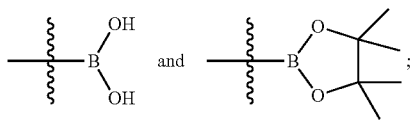

X is halogen, and preferably bromine;

$G^1$, $R^2$, $R^4$, r, s and q are as defined in formula (I).

The present invention will be further described with reference to the following examples, but the examples should not be considered as limiting the scope of the present invention.

The structures of the compounds were identified by nuclear magnetic resonance (NMR) and/or mass spectrometry (MS). NMR shifts ($\delta$) are given in $10^{-6}$ (ppm). NMR was determined by a Bruker AVANCE-400 machine. The solvents for determination were deuterated-dimethyl sulfoxide (DMSO-$d_6$), deuterated-chloroform (CDCl$_3$) and deuterated-methanol (CD$_3$OD), and the internal standard was tetramethylsilane (TMS).

MS was determined by a FINNIGAN LCQAd (ESI) mass spectrometer (manufacturer: Thermo, type: Finnigan LCQ advantage MAX).

High performance liquid chromatography (HPLC) was determined on an Agilent 1200DAD high pressure liquid chromatography spectrometer (Sunfire C18 150×4.6 mm chromatographic column), and a Waters 2695-2996 high pressure liquid chromatography spectrometer (Gimini C18 150×4.6 mm chromatographic column).

Chiral HPLC was determined on a LC-10A vp (Shimadzu) or SFC-analytical (Berger Instruments Inc.).

Yantai Huanghai HSGF254 or Qingdao GF254 silica gel plate was used as the thin-layer silica gel chromatography (TLC) plate. The dimension of the silica gel plate used in TLC was 0.15 mm to 0.2 mm, and the dimension of the silica gel plate used in product purification was 0.4 mm to 0.5 mm.

Yantai Huanghai 200 to 300 mesh silica gel was generally used as a carrier for column chromatography.

Prep Star SD-1 (Varian Instruments Inc.) or SFC-multigram (Berger Instruments Inc.) was used for chiral preparative column chromatography.

CombiFlash rapid preparation instrument used was Combiflash Rf200 (TELEDYNE ISCO).

The average kinase inhibition rates and IC$_{50}$ values were determined by a NovoStar ELISA (BMG Co., Germany).

The known starting materials of the present invention can be prepared by the known methods in the art, or can be purchased from ABCR GmbH & Co. KG Acros Organnics, Aldrich Chemical Company, Accela ChemBio Inc., or Dari chemical Company, etc.

In the examples, unless otherwise stated, the reactions were carried out under a nitrogen atmosphere or argon atmosphere.

"Argon atmosphere" or "nitrogen atmosphere" means that a reaction flask is equipped with an argon or nitrogen balloon (about 1 L).

"Hydrogen atmosphere" means that a reaction flask is equipped with a hydrogen balloon (about 1 L).

Pressurized hydrogenation reactions were performed on a Parr 3916EKX hydrogenation instrument and a Qinglan QL-500 hydrogen generator or HC2-SS hydrogenation instrument.

In hydrogenation reactions, the reaction system was generally vacuumed and filled with hydrogen, with the above operation was repeated three times.

CEM Discover-S 908860 type microwave reactor was used in microwave reactions.

In the examples, unless otherwise stated, the solution refers to an aqueous solution.

In the examples, unless otherwise stated, the reaction temperature is room temperature from 20° C. to 30° C.

The reaction process in the examples was monitored by thin layer chromatography (TLC), and the developing solvent used in the reactions, the elution system in column chromatography and the developing solvent system in thin layer chromatography for purification of the compounds included: A: dichloromethane/methanol system, B: n-hexane/ethyl acetate system, C: petroleum ether/ethyl acetate system, D: acetone, E: dichloromethane/acetone system, F: ethyl acetate/dichloromethane system, G: ethyl acetate/dichloromethane/n-hexane, H: ethyl acetate/dichloromethane/acetone. The ratio of the volume of the solvent was adjusted according to the polarity of the compounds, and a small quantity of alkaline reagent such as triethylamine or acidic reagent such as acetic acid can also be added for adjustment.

Example 1

4-(1-Cyclobutyl-3-(6-methylpyridin-2-yl)-1H-pyrazol-4-yl)-2-(4-(methylsulfonyl)phenyl)pyridine

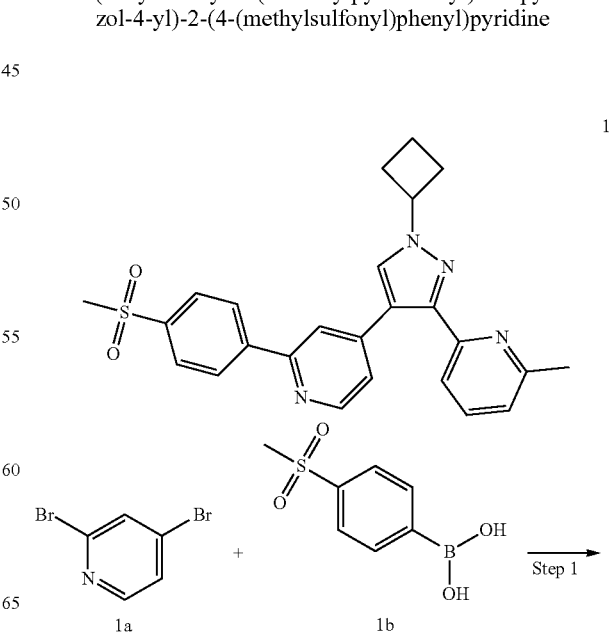

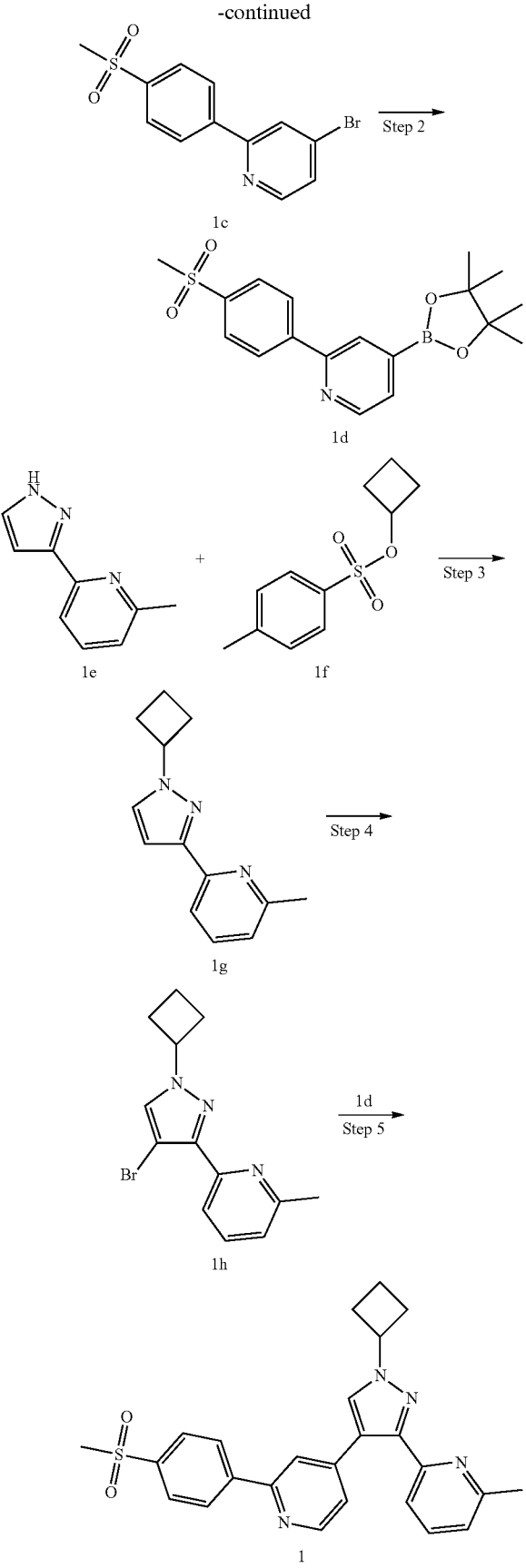

Step 1

4-Bromo-2-(4-(methylsulfonyl)phenyl)pyridine 1c 2,4-Dibromopyridine 1a (6 g, 25.33 mmol) was dissolved in 126 mL of a mixed solvent of toluene, ethanol and water (V:V:V=4:2:1), (4-(methanesulfonyl)phenyl)boronic acid 1b (5066.1 mg, 25.33 mmol), sodium carbonate (5369.1 mg, 50.66 mmol) and tetrakis(triphenylphosphine)palladium (2926.7 mg, 2.53 mmol) were added, and the reaction solution was stirred for 16 hours at 100° C. under an argon atmosphere. The reaction was monitored by LC-MS until the starting material disappeared, then the reaction stopped and cooled. The reaction solution was added with ethyl acetate and water, and extracted with ethyl acetate (80 mL×2). The organic phases were combined, dried over anhydrous sodium sulfate and filtered. The filtrate was concentrated under reduced pressure, and the resulting residue was purified by silica gel column chromatography with elution system B to obtain the title compound 1c (7.09 g, white solid, yield: 89.79%).

Step 2

2-(4-(Methanesulfonyl)phenyl)-4-(4,4,5,5-tetramethyl-1,3,2-dioxaborolan-2-yl)pyridine 1d 1c (210 mg, 0.67 mmol), bis(pinacolato)diboron (205 mg, 0.81 mmol), potassium acetate (131.5 mg, 1.34 mmol) and [1,1'-bis(diphenylphosphino)ferrocene]dichloropalladium (49 mg, 0.067 mmol) were dissolved in 10 ml of 1,4-dioxane, then the reaction solution was warmed up to 90° C. and stirred for 3 hours. The reaction solution was concentrated under reduced pressure, and the resulting residue was purified by silica gel column chromatography with elution system A to obtain the title compound 1d (130 mg, black solid, yield: 50%).

Step 3

2-(1-Cyclobutyl-1H-pyrazol-3-yl)-6-methylpyridine 1g

2-Methyl-6-(1H-pyrazol-3-yl)pyridine 1e (2.01 g, 12.6 mmol, prepared according to the known method disclosed in "*Bioorganic and Medicinal Chemistry*, 2015, 23(6), 1260-1275") was dissolved in 100 mL of N,N-dimethylformamide, then cyclobutyl toluene-4-sulfonate 1f (4.29 g, 18.9 mmol, prepared according to the method disclosed in the patent application "WO2009093029") and cesium carbonate (8.23 g, 25.3 mmol) were added, and the reaction solution was warmed up to 60° C. and stirred for 16 hours. The reaction solution was cooled to room temperature, and N,N-dimethylformamide was removed by a rotary evaporator. The residue was added with water, and extracted with ethyl acetate. The organic phases were combined, washed with saturated sodium chloride solution, dried over anhydrous sodium sulfate and filtered. The filtrate was concentrated under reduced pressure, and the resulting residue was purified by silica gel column chromatography with elution system B to obtain the title compound 1g (1.81 g, colorless oil, yield: 67.3%).

Step 4

2-(4-Bromo-1-cyclobutyl-1H-pyrazol-3-yl)-6-methylpyridine 1h 1g (91 mg, 0.43 mmol) was dissolved in 10 mL of dichloromethane, then N-bromosuccinimide (76 mg, 0.43 mmol) was added, and the reaction solution was stirred overnight at room temperature. After the reaction was completed, the reaction solution was concentrated under reduced pressure. The resulting residue was purified by silica gel column chromatography with elution system B to obtain the title compound 1h (110 mg, yellow oil, yield: 88%).

Step 5

4-(1-Cyclobutyl-3-(6-methylpyridin-2-yl)-1H-pyrazol-4-yl)-2-(4-(methylsulfonyl)phenyl)pyridine 1

1h (540 mg, 1.85 mmol), 1d (563.36 mg, 2.03 mmol), 1,1'-bis(diphenylphosphino)ferrocene (102.46 mg, 0.185 mmol), potassium carbonate (510.89 mg, 3.7 mmol) and [1,1'-bis(diphenylphosphino)ferrocene]dichloropalladium (135.24 mg, 0.185 mmol) were dissolved in 12 mL of a mixed solvent of 1,4-dioxane and water (V:V=10:1), then the reaction solution was warmed up to 80° C. and stirred for 12 hours. The reaction solution was concentrated under reduced pressure, and the resulting residue was added with water, and extracted with ethyl acetate. The organic phases were combined, dried over anhydrous sodium sulfate and filtered. The filtrate was concentrated under reduced pressure, and the resulting residue was purified by high performance liquid chromatography to obtain the title compound 1 (400 mg, yellowish white solid, yield: 48.7%).

MS m/z (ESI): 445.5 [M+1]

$^1$H NMR (400 MHz, CDCl$_3$) δ 8.66 (d, 1H), 8.11 (dd, 4H), 7.98 (s, 1H), 7.86 (s, 1H), 7.69 (t, 1H), 7.56 (d, 1H), 7.41 (s, 1H), 7.20 (d, 1H), 4.96-4.92 (m, 1H), 3.13 (s, 3H), 2.72-2.60 (nm, 4H), 2.55 (s, 3H), 2.01-1.94 (m, 2H).

Example 2

4-(1-Cyclopropyl-3-(6-methylpyridin-2-yl)-1H-pyrazol-4-yl)-2-(4-(methylsulfonyl)phenyl)pyridine

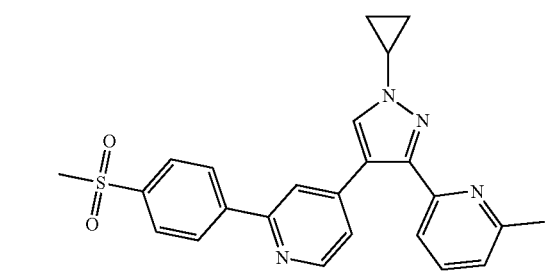

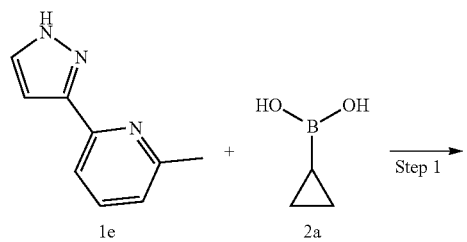

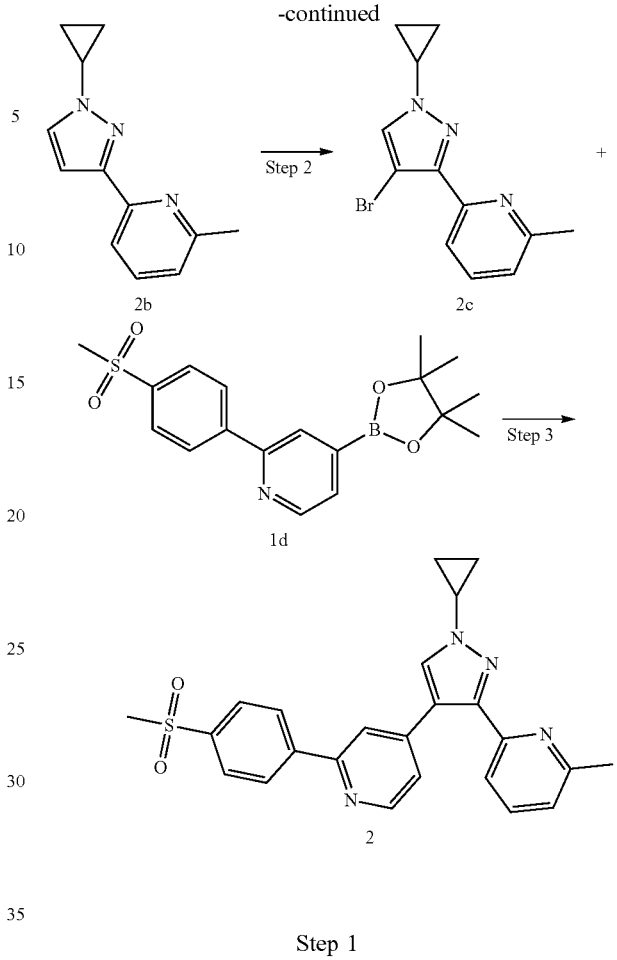

Step 1

2-(1-Cyclopropyl-1H-pyrazol-3-yl)-6-methylpyridine 2b 1e (700 mg, 4.40 mmol), cyclopropylboronic acid 2a (756 mg, 8.80 mmol), copper acetate monohydrate (1.76 g, 8.80 mmol), sodium carbonate (933 mg, 8.80 mmol) and 2,2-bipyridine (1.37 g, 8.80 mmol) were dissolved in 25 mL of 1,2-dichloroethane, then the reaction solution was warmed up to 50° C. and stirred for 16 hours. After the reaction was completed, the reaction solution was filtered, and the filtrate was concentrated under reduced pressure. The resulting residue was purified by silica gel column chromatography with elution system B to obtain the title compound 2b (440 mg, yellow viscous material, yield: 50.2%).

Step 2

2-(4-Bromo-1-cyclopropyl-1H-pyrazol-3-yl)-6-methylpyridine 2c 2b (330 mg, 1.66 mmol) was dissolved in 8 mL of dichloromethane, then N-bromosuccinimide (295 mg, 1.66 mmol) was added, and the reaction solution was stirred for 1 hour at room temperature. After the reaction was completed, the reaction solution was added with water, and extracted with dichloromethane (10 mL×3). The organic phases were combined and concentrated under reduced pressure. The resulting residue was purified by silica gel column chromatography with elution system A to obtain the title compound 2c (335 mg, yellow viscous material, yield: 72.6%).

Step 3

4-(1-Cyclopropyl-3-(6-methylpyridin-2-yl)-1H-pyrazol-4-yl)-2-(4-(methylsulfonyl)phenyl)pyridine 2

2c (40 mg, 0.144 mmol), 1d (103.5 mg, 0.288 mmol), potassium phosphate (183.4 mg, 0.864 mmol) and [1,1'-bis(diphenylphosphino)ferrocene]dichloropalladium (10.5 mg, 0.0144 mmol) were dissolved in 2 mL of 1,4-dioxane, then the reaction solution was warmed up to 90° C. and stirred for 16 hours. The reaction solution was concentrated under reduced pressure, and the resulting residue was added with water, and extracted with ethyl acetate. The organic phases were combined, dried over anhydrous sodium sulfate and filtered. The filtrate was concentrated under reduced pressure, and the resulting residue was purified by high performance liquid chromatography to obtain the title compound 2 (10 mg, yellowish white solid, yield: 16%).

MS m/z (ESI): 431.5 [M+1]

$^1$H NMR (400 MHz, CD$_3$OD) δ 8.55 (dd, 1H), 8.32 (s, 1H), 8.12-8.05 (m, 4H), 7.91 (dd, 1H), 7.82 (t, 1H), 7.53 (d, 1H), 7.37-7.34 (m, 2H), 3.86-3.81 (nm, 1H), 3.18 (s, 3H), 2.48 (s, 3H), 1.30-1.26 (m, 2H), 1.18-1.13 (m, 2H).

Example 3

4-(1-Cyclopentyl-3-(6-methylpyridin-2-yl)-1H-pyrazol-4-yl)-2-(4-(methylsulfonyl)phenyl)pyridine

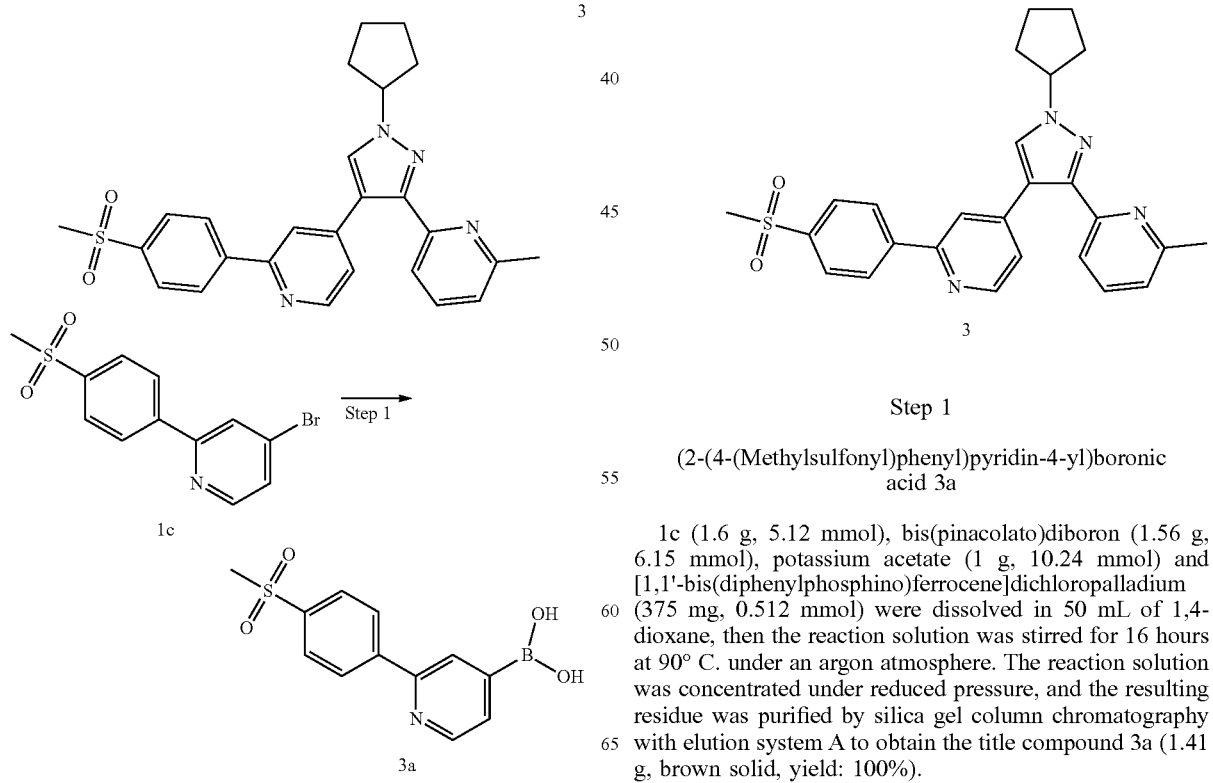

Step 1

(2-(4-(Methylsulfonyl)phenyl)pyridin-4-yl)boronic acid 3a 1c (1.6 g, 5.12 mmol), bis(pinacolato)diboron (1.56 g, 6.15 mmol), potassium acetate (1 g, 10.24 mmol) and [1,1'-bis(diphenylphosphino)ferrocene]dichloropalladium (375 mg, 0.512 mmol) were dissolved in 50 mL of 1,4-dioxane, then the reaction solution was stirred for 16 hours at 90° C. under an argon atmosphere. The reaction solution was concentrated under reduced pressure, and the resulting residue was purified by silica gel column chromatography with elution system A to obtain the title compound 3a (1.41 g, brown solid, yield: 100%).

MS m/z (ESI): 278.4 [M+1]

Step 2

2-(1-Cyclopentyl-1H-pyrazol-3-yl)-6-methylpyridine 3c 1e (700 mg, 440 mmol) was dissolved in 10 mL of N,N-dimethylformamide, then cyclopentyl toluene-4-sulfonate 3b (1,056 g, 4.40 mmol, prepared according to the method disclosed in the patent application "WO2009062990") and cesium carbonate (2.87 g, 8.80 mmol) were added, and the reaction solution was stirred at 60° C. for 2 hours. The reaction solution was cooled to room temperature, added with 50 mL of water, and extracted with ethyl acetate (50 mL×3). The organic phases were combined, dried over anhydrous sodium sulfate and filtered. The filtrate was concentrated under reduced pressure, and the resulting residue was purified by CombiFlash rapid preparation instrument with elution system B to obtain the title compound 3c (600 mg, light yellow oil, yield: 60%).

Step 3

2-(4-Bromo-1-cyclopentyl-1H-pyrazol-3-yl)-6-methylpyridine 3d 3c (600 mg, 2.64 mmol) was dissolved in 15 mL of dichloromethane, then N-bromosuccinimide (470 mg, 2.64 mmol) was added, and the reaction solution was stirred at room temperature for 1 hour. After the reaction was completed, the reaction solution was concentrated under reduced pressure. The resulting residue was purified by CombiFlash rapid preparation instrument with elution system B to obtain the title compound 3d (760 mg, light yellow oil, yield: 94.0%).

MS m/z (ESI): 306.3 [M+1]

Step 4

4-(1-Cyclopentyl-3-(6-methylpyridin-2-yl)-1H-pyrazol-4-yl)-2-(4-(methylsulfonyl)phenyl)pyridine 3

3d (61 mg, 0.2 mmol), 3a (67 mg, 0.24 mmol), 1,1'-bis(diphenylphosphino)ferrocene (11 mg, 0.02 mmol), potassium carbonate (55 rag, 0.4 mmol) and [1,1'-bis(diphenylphosphino)ferrocene]dichloropalladium (15 mg, 0.02 mmol) were dissolved in 5.5 mL of a mixed solvent of 1,4-dioxane and water (V:V=10:1), then the reaction solution was warmed up to 80° C. and stirred for 6 hours under an argon atmosphere. The reaction solution was concentrated under reduced pressure, and the resulting residue was purified by high performance liquid chromatography to obtain the title compound 3 (20 mg, white solid, yield: 21.9%).

MS m/z (ESI): 459.4 [M+1]

$^1$H NMR (400 MHz, CDCl$_3$) δ 8.68 (d, 1H), δ 8.18 (d, 2H), δ 8.08 (d, 2H), 7.84 (s, 1H), 7.70 (t, 1H), 7.60-7.56 (m, 1H), 7.35-7.30 (m, 2H), 7.21 (d, 1H), 4.89-4.78 (m, 1H), 3.14 (d, 3H), 2.54 (d, 3H), 2.36-2.29 (m, 2H), 2.22-2.15 (m, 2H), 2.01-1.92 (m, 2H), 1.87-1.78 (m, 2H).

Example 4

(S)-4-(3-(6-Methylpyridin-2-yl)-1-(tetrahydrofuran-3-yl)-1H-pyrazol-4-yl)-2-(4—(methyl sulfonyl)phenyl)pyridine

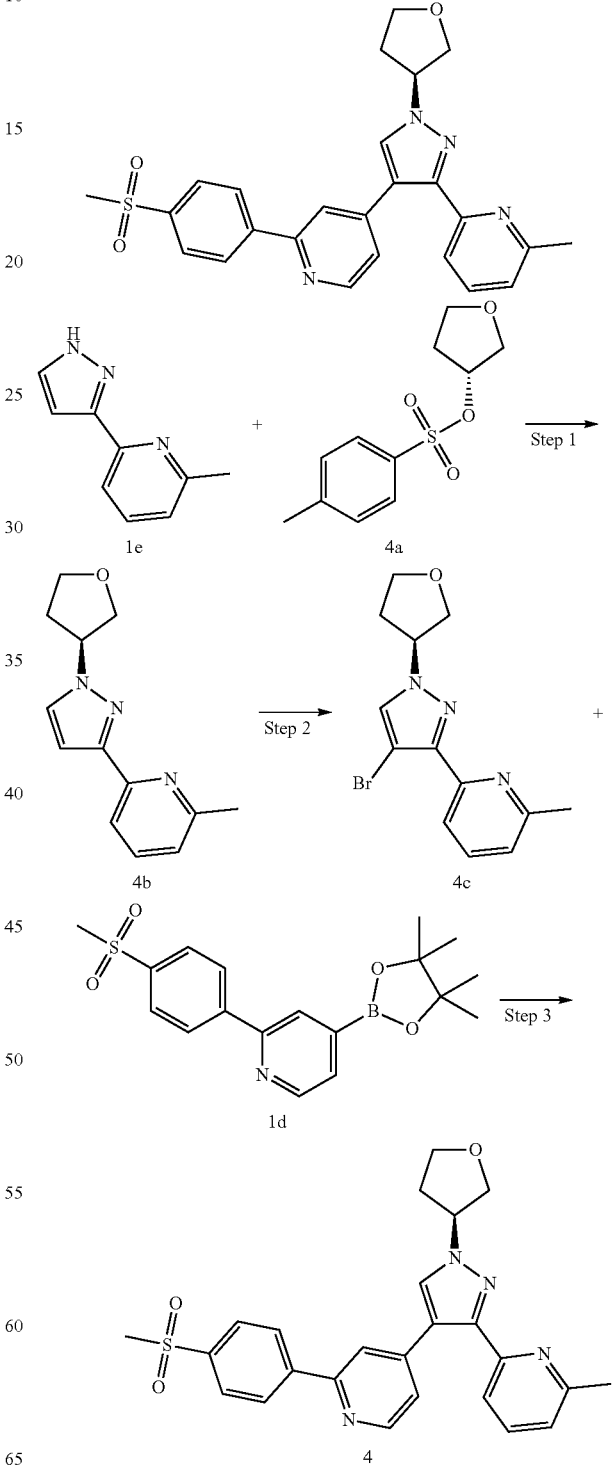

Example 5

(R)-4-(3-(6-Methylpyridin-2-yl)-1-(tetrahydrofuran-3-yl)-1H-pyrazol-4-yl)-2-(4—(methyl sulfonyl)phenyl)pyridine

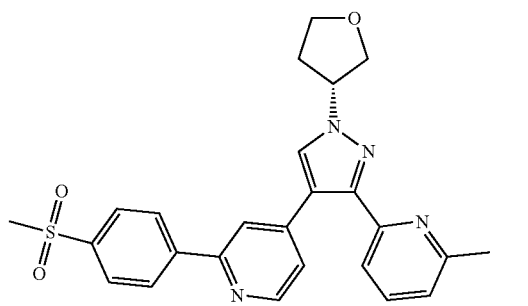

5

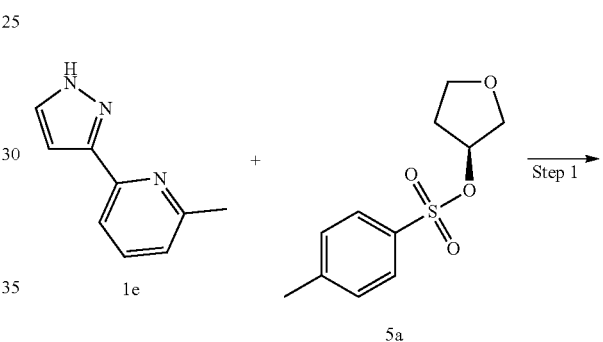

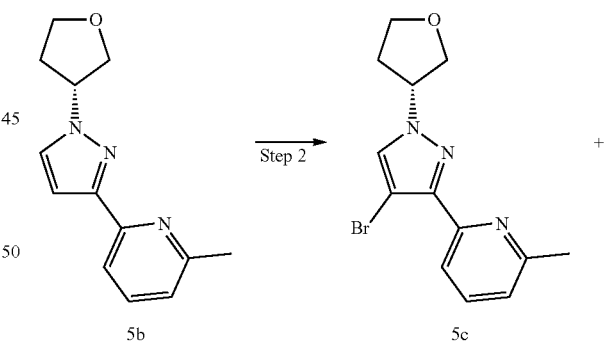

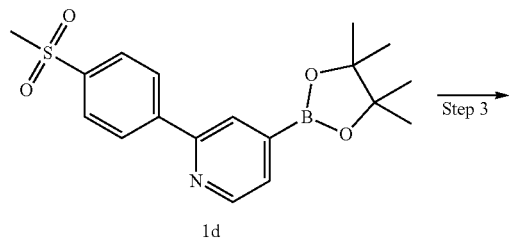

Step 1

(S)-2-Methyl-6-(1-(tetrahydrofuran-3-yl)-1H-pyrazol-3-yl)pyridine 4b 1e (328 mg, 2.06 mmol) was dissolved in 10 mL of N,N-dimethylformamide, then (R)-tetrahydrofuran-3-yl toluene-4-sulfonate 4a (500 mg, 2.06 mmol, prepared according to the method disclosed in the patent application "WO2016021192") and cesium carbonate (1.3 g, 4.12 mmol) were added, and the reaction solution was stirred at 60° C. for 2 hours. The reaction solution was concentrated under reduced pressure, and the resulting residue was added with water, and extracted with ethyl acetate. The organic phases were combined, dried over anhydrous sodium sulfate and filtered. The filtrate was concentrated under reduced pressure to obtain the crude title compound 4b (370 mg, colorless transparent oil), which was used directly in the next step without purification.

Step 2

(S)-2-(4-Mromo-1-(tetrahydrofuran-3-yl)-1H-pyrazol-3-yl)-6-methylpyridine 4c The crude product 4b (800 mg, 3.47 mmol) was dissolved in 18 mL of dichloromethane, then N-bromosuccinimide (741.76 mg, 4.16 mmol) was added, and the reaction solution was stirred for 1 hour at room temperature. After the reaction was completed, the reaction solution was added with water, and extracted with dichloromethane. The organic phases were combined, dried over anhydrous sodium sulfate and filtered. The filtrate was concentrated under reduced pressure, and the resulting residue was purified by silica gel column chromatography with elution system A to obtain the title compound 4c (123 mg, yellowish white solid, yield: 11.39%).

Step 3

(S)-4-(3-(6-Methylpyridin-2-yl)-1-(tetrahydrofuran-3-yl)-1H-pyrazol-4-yl)-2-(4—(methyl sulfonyl)phenyl)pyridine 4

4c (123 mg, 0.4 mmol) was dissolved in 5.5 mL of a mixed solvent of 1,4-dioxane and water (V:V=10:1), then 1d (166 mg, 0.6 mmol), 1,1'-bis(diphenylphosphino)ferrocene (22 mg, 0.04 mmol), potassium carbonate (110 mg, 0.8 mmol) and [1,1'-bis(diphenylphosphino)ferrocene]dichloropalladium (29 mg, 0.04 mmol) were added, and the reaction solution was warmed up to 80° C. and stirred for 16 hours under an argon atmosphere. The reaction solution was concentrated under reduced pressure, and the resulting residue was purified by silica gel column chromatography with elution system A to obtain the title compound 4 (20 mg, yellow solid, yield: 10.86%).

MS m/z (ESI): 461.5 [M+1]

$^1$H NMR (400 MHz, CD$_3$OD) δ 8.54 (d, 1H), 8.30 (s, 1H), 8.06 (q, 4H), 7.92 (s, 1H), 7.79 (t, 1H), 7.55 (d, 1H), 7.37-7.31 (m, 2H), 5.17 (m, 1H), 4.18 (q, 2H), 4.12 (m, 1H), 3.98 (t, 1H), 3.13 (s, 3H), 2.57-2.50 (m, 2H), 2.49 (s, 3H).

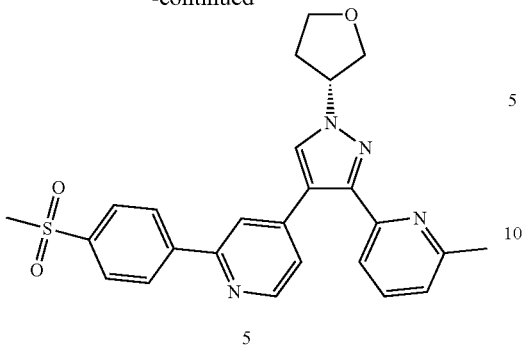

Step 1

(R)-2-Methyl-6-(1-(tetrahydrofuran-3-yl)-1H-pyrazol-3-yl)pyridine 5b 1e (637 mg, 4.0 mmol) was dissolved in 20 mL of N,N-dimethylformamide, then (S)-tetrahydrofuran-3-yl toluene-4-sulfonate 5a (1.45 g, 6.0 mmol, prepared according to the method disclosed in the patent application "WO2014049133") and cesium carbonate (2.61 g, 8.0 mmol) were added, and the reaction solution was stirred at 60° C. for 16 hours. The reaction solution was concentrated under reduced pressure, and the resulting residue was purified by CombiFlash rapid preparation instrument with elution system B to obtain the title compound 5b (610 mg, colorless oil, yield: 66.5%).

Step 2

(R)-2-(4-Bromo-1-(tetrahydrofuran-3-yl)-1H-pyrazol-3-yl)-6-methylpyridine 5c 5b (600 mg, 2.62 mmol) was dissolved in 30 mL of dichloromethane, then N-bromosuccinimide (466 mg, 2.62 mmol) was added, and the reaction solution was stirred for 16 hours at room temperature. After the reaction was completed, the reaction solution was concentrated under reduced pressure. The resulting residue was purified by CombiFlash rapid preparation instrument with elution system B to obtain the title compound 5c (795 mg, yellow oil, yield: 98.6%).

Step 3

(R)-4-(3-(6-Methylpyridin-2-yl)-1-(tetrahydrofuran-3-yl)-1H-pyrazol-4-yl)-2-(4—(methyl sulfonyl)phenyl)pyridine 5

5c (100 mg, 0.32 mmol) was dissolved in 15 mL of a mixed solvent of 1,4-dioxane and water (V:V=10:1), then 1d (135 mg, 0.49 mmol), 1,1'-bis(diphenylphosphino)ferrocene (18 mg, 0.032 mmol), potassium carbonate (88 mg, 0.64 mmol) and [1,1'-bis(diphenylphosphino)ferrocene]dichloropalladium (23 mg, 0.032 mmol) were added, and the reaction solution was warmed up to 80° C. and stirred for 16 hours under an argon atmosphere. After the reaction was completed, the reaction solution was concentrated under reduced pressure. The resulting residue was purified by CombiFlash rapid preparation instrument with elution system A to obtain the title compound 5 (58 mg, light brown solid, yield: 38.9%).

MS m/z: (ESI): 461.5 [M+1]

$^1$H NMR (400 MHz, CDCl$_3$) δ 8.66-8.65 (d, 1H), 8.16-8.14 (d, 2H), 8.06-8.04 (d, 2H), 7.92 (s, 1H), 7.88 (s, 1H), 7.68-7.64 (t, 1H), 7.51-7.49 (d, 1H), 7.36-7.34 (dd, 1H), 7.20-7.18 (d, 1H), 5.19 (m, 1H), 4.19-4.24 (m, 2H), 4.14-4.10 (m, 1H), 4.03-4.01 (m, 1H). 3.13 (s, 3H), 2.66-2.57 (m, 1H), 2.55 (s, 3H), 2.51-2.42 (m, 1H).

Example 6

4-(3-(6-Methyl pyridin-2-yl)-1-(oxetan-3-yl)-1H-pyrazol-4-yl)-2-(4-(methylsulfonyl)phenyl)pyridine

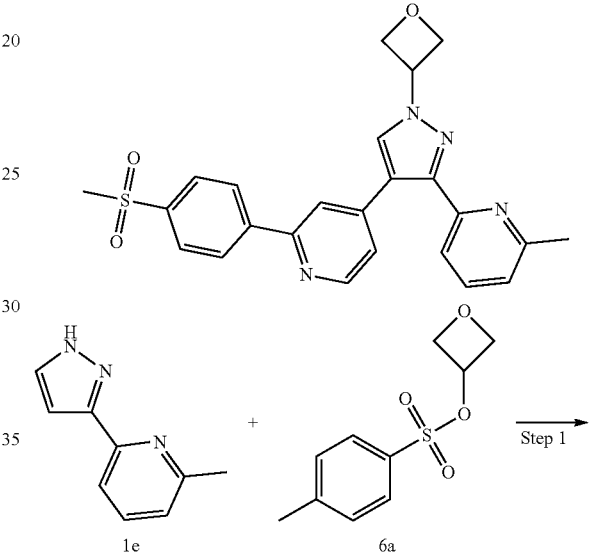

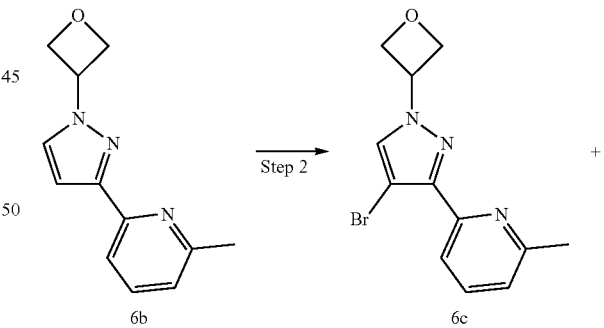

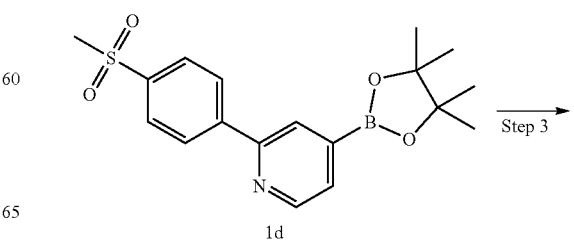

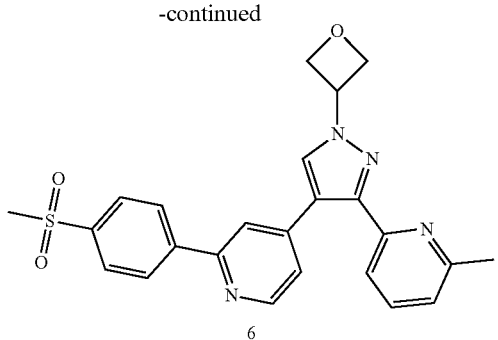

6

Step 1

2-Methyl-6-(1-(oxetan-3-yl)-1H-pyrazol-3-yl)pyridine 6b 1e (749 mg, 4.7 mmol) was dissolved in 15 mL of N,N-dimethylformamide, then oxetan-3-yl toluene-4-sulfonate 6a (1.61 g, 7.05 mmol, prepared according to the method disclosed in the patent application "WO2013056070") and cesium carbonate (3.06 g, 9.4 mmol) were added, and the reaction solution was stirred for 3 hours at 60° C. The reaction solution was concentrated under reduced pressure, and the resulting residue was purified by CombiFlash rapid preparation instrument with elution system A to obtain the title compound 6b (420 mg, light yellow oil, yield: 41.6%).

Step 2

2-(4-Bromo-1-(oxetan-3-yl)-1H-pyrazol-3-yl)-6-methylpyridine 6c 6b (420 rag, 1.95 mmol) was dissolved in 30 mL of dichloromethane, then N-bromosuccinimide (347 mg, 1.95 mmol) was added, and the reaction solution was stirred for 16 hours at room temperature. After the reaction was completed, the reaction solution was concentrated under reduced pressure. The resulting residue was purified by CombiFlash rapid preparation instrument with elution system A to obtain the title compound 6c (479 mg, light yellow oil, yield: 83.4%).

Step 3

4-(3-(6-Methylpyridin-2-yl)-1-(oxetan-3-yl)-1H-pyrazol-4-yl)-2-(4-(methylsulfonyl)phenyl)pyridine 6

6c (50 mg, 0.17 mmol) was dissolved in 5.5 mL of a mixed solvent of 1,4-dioxane and water (V:V=10:1), then 1d (91.6 mg, 025 mmol), 1,1'-bis(diphenylphosphino)ferrocene (9.42 mg, 0.02 mmol), potassium carbonate (46.99 mg, 0.34 mmol) and [1,1'-bis(diphenylphosphino)ferrocene]dichloropalladium (12.44 mg, 0.02 mmol) were added, and the reaction solution was warmed up to 80° C. and stirred for 18 hours under an argon atmosphere. The reaction was monitored by LC-MS until the starting material disappeared, then the reaction was stopped. The reaction solution was cooled and concentrated to remove most of the solvent. The residue was added with 10 mL of water, and extracted with ethyl acetate (10 mL×3). The organic phases were combined, washed with saturated sodium chloride solution (10 mL×2), dried over anhydrous sodium sulfate and filtered. The filtrate was concentrated under reduced pressure, and the resulting residue was purified by silica gel column chromatography with elution system A to obtain the title compound 6 (41 mg, yellow solid, yield: 52.43%).

MS m/z (ESI): 447.4 [M+1]

$^1$H NMR (400 MHz, CDCl$_3$) 8.65 (d, 1H), 8.07 (dd, 4H), 7.99 (s, 1H), 7.91 (s, 1H), 7.64 (t, 1H), 7.54 (d, 1H), 7.34 (d, 1H), 7.18 (d, 1H), 5.64-5.58 (m, 1H), 5.17-5.13 (m, 4H), 3.10 (s, 3H), 2.51 (s, 3H).

Example 7

4-(4-(1-Cyclopropyl-3-(6-methylpyridin-2-yl)-1H-pyrazol-4-yl)pyridin-2-yl)benzonitrile 7

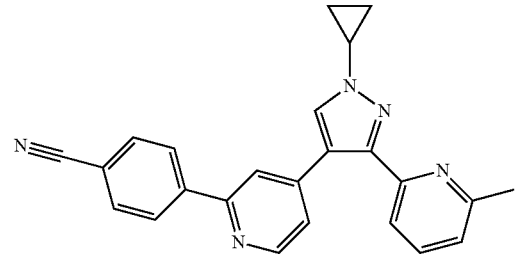

7

In accordance with the synthetic route of Example 2, the starting compound 1d used in Step 3 was replaced with 4-(4-(4,4,5,5-tetramethyl-1,3,2-dioxaborolan-2-yl)pyridin-2-yl)benzonitrile (prepared according to the method disclosed in the patent application "KR20160025776"), accordingly, the title compound 7 (10 mg) was prepared.

MS m/z (ESI): 378.4 [M+1]

$^1$H NMR (400 MHz, CD$_3$OD) δ 8.67-8.66 (d, 1H), 8.48 (s, 1H), 8.25-8.21 (m, 1H), 8.13-8.11 (m, 3H), 7.91-7.89 (d, 2H), 7.75-7.72 (m, 2H), 7.56-7.54 (d, 1H), 3.98-3.92 (m, 1H), 2.77 (s, 31H), 1.35-1.28 (m, 21H), 1.22-1.18 (m, 2H).

Example 8

(R)-4-(3-(6-Methylpyridin-2-yl)-1-(1-(methylsulfonyl)pyrrolidin-3-yl)-1H-pyrazol-4-yl)-2-(4-(methylsulfonyl)phenyl)pyridine 8

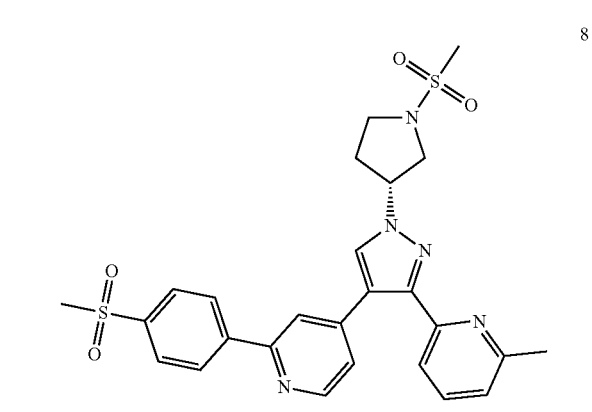

8

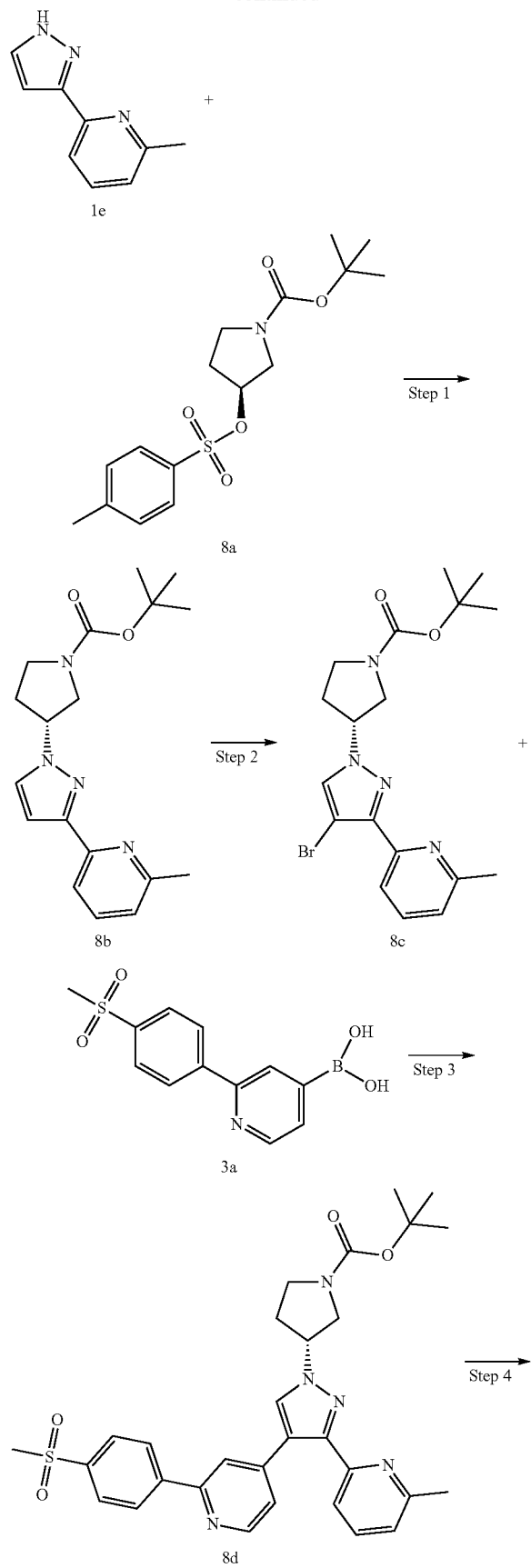

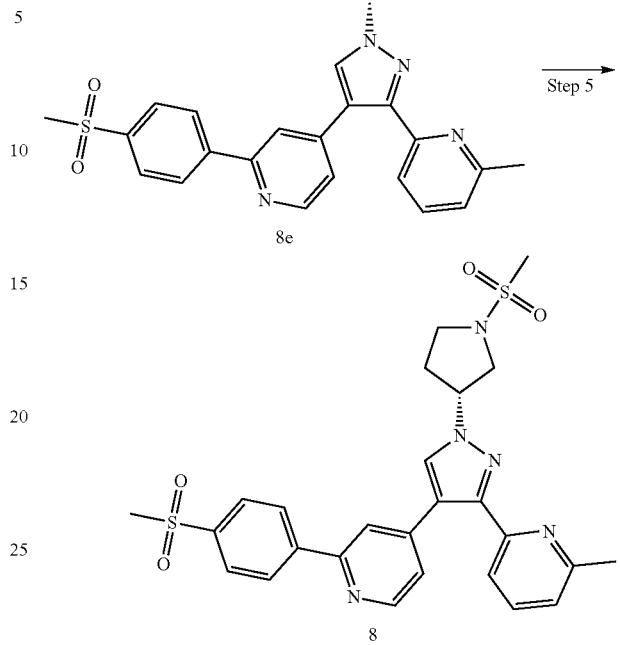

Steps 1 to 3

Tert-butyl (R)-3-(3-(6-methylpyridin-2-yl)-4-(2-(4-(methylsulfonyl)phenyl)pyridin-4-yl)-1H-pyrazol-1-yl)pyrrolidine-1-carboxylate 8d In accordance with the synthetic route of Example 3, the starting compound 3b used in Step 2 was replaced with tell-butyl (S)-3-(tosyloxy)pyrrolidine-1-carboxylate 8a (prepared according to the method disclosed in the patent application "WO2016034134"), accordingly, the title compound 8d (190 mg) was prepared.

Step 4

(R)-4-(3-(6-Methylpyridin-2-yl)-1-(pyrrolidin-3-yl)-1 n-pyrazol-4-yl)-2-(4-(methylsulfonyl)phenyl) pyridine hydrochloride 8e Compound 8d (190 mg, 0.3395 mmol) was dissolved in 10 mL of ethyl acetate, then a solution of 4M hydrogen chloride in 1,4-dioxane (0.42 mL, 1.69 mmol) was added, and the reaction solution was stirred for 4 hours. The reaction solution was concentrated under reduced pressure to obtain the crude title compound 8e (200 mg), which was used directly in the next step without purification.

Step 5

(R)-4-(3-(6-Methylpyridin-2-yl)-1-(1-(methylsulfonyl)pyrrolidin-3-yl)-1H-pyrazol-4-yl)-2-(4-(methylsulfonyl)phenyl)pyridine 8

The crude compound 8e (100 mg, 0.2176 mmol) was dissolved in 3 mL of pyridine, then mesyl chloride (74.8 mg, 0.6528 mmol) was added dropwise, and the reaction solution was stirred for 16 hours. The reaction solution was concentrated under reduced pressure, added with 20 mL of saturated copper sulfate solution, and extracted with ethyl acetate (10 mL×3). The organic phases were combined to obtain the title compound 8 (20 mg, yield: 17.1% w).

MS m/z (ESI): 538.5 [M+1]

$^1$H NMR (400 MHz, CD$_3$OD) δ 8.55-8.54 (d, 1H), 8.35 (s, 1H), 8.12-8.10 (m, 2H), 8.06-8.04 (d, 2H), 7.93 (s, 1H), 7.82-7.78 (m, 1H), 7.56-7.54 (d, 1H), 7.39-7.37 (dd, 1H), 7.33-7.31 (d, 1H), 5.22-5.15 (m, 1H), 3.93-3.87 (m, 2H), 3.76-3.69 (m, 1H), 3.62-3.56 (m, 1H), 3.17 (s, 3H), 2.94 (s, 3H), 2.62-2.57 (m, 2H), 2.45 (s, 3H).

TEST EXAMPLES

Biological Assay

Test Example 1. Determination of the Inhibition Effect of the Compounds of the Present Invention on TGFβRI Kinase Activity The inhibition effect of TGFβRI kinase activity in vitro was determined by the following method.

The inhibition effect of the compounds of the present invention on TGFβRI kinase ALK5 activity was determined by the following experimental method:

TGFβRI kinase assay kit (V4093, Promega) was used to assay enzyme activity. 2 μl of enzyme solution (the final concentration of enzyme in the reaction system was 2 ng/μL) formulated with reaction buffer (40 mM Tris pH 7.5, 20 mM MgCl$_2$, 0.1 mg/ml BSA), 1 μl of a 3-fold gradient dilution of the compounds dissolved in 5% DMSO, and 2 μl of a mixed solution of ATP and TGFβRI substrate peptide (the final concentration of ATP was 50 μM, and the final concentration of substrate was 0.2 μg/μL) were added successively to a 384-well plate (4514, Corning). After reaction at 27° C. for 2.5 hours, 5 μl of ADP-Glo solution in the kit was added to each well, then the plate was placed at 27° C. for 40 minutes. 10 μl of kinase assay reagent was then added to each well, then the plate was placed at 27° C. for 30 minutes. The chemiluminescence signal values were measured with a Victor 3 (PerkinElmer) multi-function microplate reader. The IC$_{50}$ values of the compounds for enzyme inhibition were calculated using Graphpad prism software based on each concentration of the compound and the corresponding signal value thereof.

The biological activity of the compounds of the present invention was determined by the above test, and the resulting IC$_{50}$ values are shown in Table 1 below.

TABLE 1

| IC$_{50}$ of inhibition effect of the compounds of the present invention on TGFβRI kinase ALK5 activity | |
|---|---|
| Example No. | IC$_{50}$ (nM) |
| 1 | 208 |
| 2 | 270 |
| 3 | 241 |
| 8 | 370 |

Conclusion: The compounds of the examples of the present invention have a significant inhibition effect on the TGFβRI kinase ALK5 activity.

Test Example 2. Determination of the Inhibition Effect of the Compounds of the Present Invention on VEGFR2 Kinase Activity The inhibition effect of VEGFR2 kinase activity in vitro was determined by the following method.

The inhibition effect of the compounds of the present invention on VEGFR2 kinase activity was determined by the following experimental method:

Z'-LYTEC® Kinase Assay Kit—Tyrosine 1 Peptide (PV3190, Invitrogen) was used to assay enzyme activity. 5 μl of recombinant human VEGFR2 enzyme (PV3660, Invitrogen) and VEGFR2 substrate polypeptide (in the reaction system, the final concentration of enzyme was 0.14 ng/μL, and the final concentration of substrate was 2 μM) formulated with reaction buffer (50 mM HEPES pH7.5, 10 mM MgCl$_2$, 1 mM EGTA, 0.05% BRIJ-35), 2.5 μl of a 2-fold gradient dilution of the compounds dissolved in 5% DMSO, and 2.5 μL of ATP solution (the final concentration of ATP was 50 μM) were added successively to a 384-well plate (4513, Corning). After reaction at 25° C. for 2 hours, 5 μL of detection reagent was added to each well. After the plate was placed at 25° C. for 1 hour, the fluorescence signal values at emission wavelengths of 445 nm and 520 nm were measured with a NOVOstar (BMG) multi-function microplate reader. The IC$_{50}$ values of the compounds for enzyme inhibition were calculated using Graphpad prism software based on each concentration of the compound and the corresponding signal value thereof.

The biological activity of the compounds of the present invention was determined by the above test, and the resulting IC$_{50}$ values are shown in Table 2 below

TABLE 2

| IC$_{50}$ of inhibition effect of the compounds of the present invention on VEGFR2 kinase activity | |
|---|---|
| Example No. | IC$_{50}$ (μM) |
| 1 | 2.5 |
| 2 | 4.2 |

Conclusion: The compounds of the examples of the present invention have a weak inhibition effect on VEGFR2 kinase activity, indicating that the compounds of the examples of the present invention have a selective inhibition effect on TGFβRI kinase.

Test Example 3. Determination of the Inhibition Effect of the Compounds of the Present Invention on p38α Kinase Activity The inhibition of p38α kinase activity in vitro was determined by the following method.

The inhibition effect of the compounds of the present invention on p38α kinase activity was determined by the following experimental method:

p38α kinase assay kit (V9591, Promega) was used to assay enzyme activity. 2 μl of enzyme solution (the final concentration of enzyme in the reaction system was 0.5 ng/μL) formulated with reaction buffer (40 mM Tris pH 7.5, 20 mM MgCl$_2$, 0.1 mg/ml BSA), 1 μl of a 3-fold gradient dilution of the compounds dissolved in 5% DMSO, and 2 μl of a mixed solution of ATP and p38 substrate peptide (the final concentration of ATP was 50 μM, and the final concentration of substrate was 0.2 μg/μL) were added successively to a 384-well plate (4514, Corning). After reaction at 27° C. for 2.5 hours, 5 μl of ADP-Glo solution in the kit was added to each well, then the plate was placed at 27° C. for 40 minutes. 10 μl of kinase assay reagent was then added to each well, then the plate was placed at 27° C. for 30 minutes. The chemiluminescence signal values were measured with a Victor 3 (PerkinElmer) multi-function microplate reader. The $IC_{50}$ values of the compounds on enzyme inhibition were calculated using Graphpad prism software based on each concentration of the compound and the corresponding signal value thereof.

The biological activity of the compounds of the present invention was determined by the above test, and the resulting $IC_{50}$ values are shown in Table 3 below

TABLE 3

$IC_{50}$ of inhibition effect of the compounds of the present invention on p38α kinase activity

| Example No. | $IC_{50}$ (μM) |
| --- | --- |
| 1 | 2.2 |
| 2 | 1.0 |

Conclusion: The compounds of the examples of the present invention have a weak inhibition effect on p38α kinase activity, indicating that the compounds of the examples of the present invention have a selective inhibition effect on TGFβRI kinase.

Test Example 4. Determination of the Inhibition Effect of the Compounds of the Present Invention on RIPK2 Kinase Activity The inhibition of RIPK2 kinase activity in vitro was determined by the following method.

The inhibition effect of the compounds of the present invention on RIPK2 kinase activity was determined by the following experimental method:

RIPK2 kinase assay kit (V4084, Promega) was used to assay enzyme activity. 2 μl of RIPK2 enzyme solution (the final concentration of enzyme in the reaction system was 0.5 ng/μL) formulated with reaction buffer (40 mM Tris pH 7.5, 20 mM $MgCl_2$, 0.1 mg/ml BSA), 1 μl of a 3-fold gradient dilution of Compound 1 dissolved in 5% DMSO, and 2 μl of a mixed solution of ATP and MBP substrate peptide (the final concentration of ATP was 50 μM, and the final concentration of substrate was 0.2 μg/μL) were added successively to a 384-well plate (4514, Corning). After reaction at 27° C. for 2.5 hours, 5 μl of ADP-Glo solution in the kit was added to each well, then the plate was placed at 27° C. for 40 minutes. 10 μl of kinase assay reagent was then added to each well, then the plate was placed at 27° C. for 30 minutes. The chemiluminescence signal values were measured with a Victor 3 (PerkinElmer) multi-function microplate reader. The $IC_{50}$ values of the compounds for enzyme inhibition were calculated using Graphpad prism software based on each concentration of the compound and the corresponding signal value thereof.

The biological activity of the compounds of the present invention was determined by the above test, and the resulting $IC_{50}$ values are shown in Table 4 below.

TABLE 4

$IC_{50}$ of inhibition effect of the compounds of the present invention on RIPK2 kinase activity

| Example No. | $IC_{50}$ (μM) |
| --- | --- |
| 1 | 1.2 |

Conclusion: The compounds of the examples of the present invention have a weak inhibition effect on RIPK2, indicating that the compounds of the examples of the present invention have a selective inhibition effect on TGFβRI kinase.

Test Example 4. Determination of the Inhibition of the Compounds of the Present Invention on NIH3T3 Cell Proliferation The inhibition effect of the compounds of the present invention on NIH3T3 cell proliferation was determined by the following in vitro test.

The inhibition effect of the compounds of the present invention on NIH3T3 cell proliferation was determined by the following experimental method:

On a 96-well white plate with transparent bottom (3903, Corning), 100 μL of NIH3T3 cell (GNM6, Cell Bank of Typical Culture Collection Committee of Chinese Academy of Sciences) was seeded in a DMEM medium containing 10% FBS (SH1-30243.01, GE) in each well. The seeding density is 2000 cells/well. The cells were incubated overnight at 37° C., in 5% $CO_2$. After overnight incubation, each well was replaced with 90 μL of DMEM medium containing 0.5%0 FBS. 10 μl of a 3-fold gradient dilution of the compounds with DMEM medium containing 0.5% FBS was then added, and the plate was incubated for 72 hours in a cell incubator at 37° C., in 5% $CO_2$. Finally, 50 μL of CellTiter-Glo (G7573, Promega) was added to each well. After incubation for 10 minutes at room temperature, the chemiluminescence signal values were measured with a Victor 3 microplate reader (PerkinElmer). The $IC_{50}$ values of the compounds were calculated using Graphpad Prism software based on each concentration of the compound and the corresponding signal value thereof.

The biological activity of the compounds of the present invention was determined by the above assay, and the calculated $IC_{50}$ values are shown in Table 4 below:

TABLE 4

$IC_{50}$ of the compounds of the present invention on the inhibition of NIH3T3 cell proliferation

| Example No. | $IC_{50}$ (nM) | Maximum inhibition rate (%) |
| --- | --- | --- |
| 1 | 88 | 105% |
| 2 | 194 | 107% |
| 3 | 366 | 105% |
| 8 | 490 | 114% |

Conclusion: The compounds of the present invention have a significant inhibition activity on NIH3T3 cell proliferation.

Test Example 5. Determination of the Inhibition Effect of the Compounds of the Present Invention on Smad Signaling Pathway of TGFβRI The inhibition effect of the compounds of the present invention on Smad signaling pathway of TGFβRI was determined by the following in vitro test.

The inhibition effect of the compounds of the present invention on Smad signaling pathway of TGFβRI was determined by the following experimental method:

On a 96-well plate, 100 μL of HepG2 cell (TCHu 72, Cell Bank of Typical Culture Collection Committee of Chinese Academy of Sciences) was seeded on an EMEM medium containing 10% FBS (42360-099, Gibco) in each well. The seeding density is $2.5 \times 10^4$ cells/well. The cells were incubated overnight at 37° C., in 5% $CO_2$. Each well was replaced with fresh EMEM medium containing 10% FBS. 0.1 μg of 3TP-lux plasmid (11767, Biovector Science Lab, Inc.) was transfected in each well. The cells were further incubated for 24 hours at 37° C., in 5% $CO_2$. Each well was replaced with 90 μL of EMEM medium containing 0.5% FBS, then the cells were starved for 6 hours. The compounds were formulated as a 20 mM stock solution, which was diluted in gradient to a 400× concentration with 100% DMSO, and further 40-fold diluted with EMEM containing 0.5% FBS. The cell culture plate was taken out, then 10 μl of diluted compound or control (0.25% DMSO) was added to each well respectively. The plate was shaken gently, then incubated for 18 hours in an incubator at 37° C., in 5% $CO_2$. Finally, 100 μl of detection reagent ONE-Glo™ Luciferase Assay (E6110, Promega) was added to each well, and the plate was placed in dark at room temperature for 10 minutes. The chemiluminescence signal values were measured with a Victor 3.0 (PerkinElmer). The $IC_{50}$ values of the compounds were calculated using Graphpad Prism software based on each concentration of the compound and the corresponding signal value thereof.

The biological activity of the compounds of the present invention was determined by the above assay, and the calculated $IC_{50}$ values are shown in Table 5 below:

TABLE 5

$IC_{50}$ of the compounds of the present invention on the inhibition of Smad signaling pathway of TGFβRI

| Example No. | $IC_{50}$ (nM) | Maximum inhibition rate (%) |
|---|---|---|
| 1 | 77 | 101% |
| 2 | 174 | 100% |
| 3 | 57 | 101% |
| 7 | 168 | 98% |
| 8 | 218 | 98% |

Conclusion: The compounds of the present invention have a significant inhibition activity on Smad signaling pathway of TGFβRI.

Pharmacokinetics Evaluation

Test Example 6. Pharmacokinetics Assay of the Compounds of the Present Invention 1. Abstract Rats were used as test animals. The drug concentration in plasma at different time points was determined by LC/MS/MS method after intragastrical administration of the compounds of Examples 1 and 2 to rats. The pharmacokinetic behavior of the compounds of the present invention was studied and evaluated in rats.

2. Test Protocol 2.1 Test Drugs

Compounds of Examples 1 and 2.

2.2 Test Animals

Eight healthy adult Sprague-Dawley (SD) rats (half male and half female) were purchased from SINO-BRITISH SIPPR/BK LAB. ANIMAL LTD., CO, with Certificate No.: SCXK (Shanghai) 2008-0016, and equally divided into 2 groups (4 rats per group).

2.3 Preparation of the Drugs

A certain amount of the test drug was weighed, and added with 5% by volume of DMSO, 5% by volume of Tween 80, and 90% by volume of physiological saline to prepare a 0.2 mg/mL colorless, clear and transparent solution.

2.4 Administration

After an overnight fast, SD rats were administered intragastrically the test drugs at an administration dosage of 2.0 mg/kg and an administration volume of 10.0 mL/kg.

3. Process

The rats were intragastrically administered the compounds of Examples 1 and 2. 0.2 mL of blood was taken from the orbital sinus before administration and at 0.5, 1.0, 2.0, 4.0, 6.0, 8.0, 11.0 and 24.0 hours after administration. The samples were stored in heparinized tubes, and centrifuged for 10 minutes at 4° C. at 3,500 rpm to separate the blood plasma. The plasma samples were stored at −20° C. The rats were fed 2 hours after administration.

The content of the test compounds in the plasma of rats after intragastrical administration of the test drugs at different concentrations was determined: 25 μL of rat plasma at each time after administration was taken, added with 30 μL (100 ng/mL) of the internal standard solution of camptothecin and 225 μL of acetonitrile, vortex-mixed for 5 minutes, and centrifuged for 10 minutes (3600 rpm). 5.0 μL of the supernatant was taken from the plasma samples for LC/MS/MS analysis.

4. Results of Pharmacokinetic Parameters

Pharmacokinetic parameters of the compounds of the present invention are shown below:

| | Pharmacokinetics assay (2 mg/g) | | | | | |
|---|---|---|---|---|---|---|
| No. | Plasma concentration Cmax (μg/mL) | Area under curve AUC (ng/mL*h) | Half-life T1/2 (h) | Residence time MRT (h) | Clearance CLz/F (ml/min/kg) | Apparent distribution volume Vz/F (ml/kg) |
| Example 1 | 1833 ± 941 | 3274 ± 1472 | 1.23 ± 0.33 | 1.72 ± 0.21 | 11.9 ± 5.2 | 1198 ± 437 |
| Example 2 | 2023 ± 666 | 8061 ± 5286 | 1.99 ± 0.95 | 3.06 ± 0.87 | 5.33 ± 2.65 | 872 ± 536 |

Conclusion: The compounds of the present invention are well absorbed, and have a significant pharmacokinetic advantage.

Toxicity Assay

Test Example 7. Toxicity Assay of TGFβ Inhibitor Repeatedly Intragastrically Administered to SD Rats for 7 Days 1. Test Purpose Evaluation of the toxicity of TGFβ inhibitor Compound 1 repeatedly intragastrically administered to SD rats for 7 days.

2 Test Drug

Compound 1, purity: 100%, white solid

Salt molecular weight: 444.5, free base molecular weight: 444.5 (based on free base)

Storage condition: room temperature

3. Test Protocol and Test Method 3.1. Test Animals and Feeding Conditions

Twenty six SPF grade SD rats (approximately 180~200 g, 6-7 weeks old, half male and half female) were purchased from Shanghai Jiesijie Laboratory Animal Co., Ltd.

Feeding conditions: SPF grade, animals were housed in plastic transparent rat cages, and 2-3 rats per cage. Room temperature: 20-26° C., relative humidity: 40-70%. 12 hours light/12 hours dark were alternated. The rats had free access to pellet feed for rats. The rats had free access to high-temperature sterilized water via drinking bottle.

3.2. Animal Grouping:

The animals were divided randomly into 5 groups, i.e. solvent control group, compound 1—30 mg/kg group, compound 1—100 mg/kg group, and the corresponding toxicokinetics groups. There were 6 rats in solvent control group, compound 1—30 mg/kg group and compound 1—100 mg/kg group, and there were 4 rats in each corresponding toxicokinetics groups, half male and half female.

| Group | Test sample | Concentration (mg/mL) | Animal No. Male | Female |
|---|---|---|---|---|
| Solvent control group | Solvent | 0 | 1~3 | 4~6 |
| 30 mg/kg group | Compound 1 | 3 | D1~D3 | D4~D6 |
| 100 mg/kg group | Compound 1 | 10 | E1~E3 | E4~E6 |
| 30 mg/kg toxicokinetics (TK) group | Compound 1 | 3 | $D_{TK}1$~$D_{TK}2$ | $D_{TK}3$~$D_{TK}4$ |
| 100 mg/kg toxicokinetics (TK) group | Compound 1 | 10 | $E_{TK}1$~$E_{TK}2$ | $E_{TK}3$~$E_{TK}4$ |

3.3. Test Method

The dose of the test compound in the 7-day toxicity assay in rats was 30 and 100 mg/kg (qd), respectively, and the administration was continued for 7 days. Administration route: intragastrical administration, administration dosage: 10 ml/kg, administration frequency and administration period: daily morning administration, continuous administration for 7 days.

3.4. Data. Representation and Statistical Processing

The results of various indicators were entered into computer Excel and entered and processed by SPSS software package.

The clinical symptom, food intake and anatomical gross observation were not processed statistically, and only the observation data of the observation items in the protocol were listed. Indicators such as body weight, organ weight, and clinical examination were processed statistically using SPSS.

4. Results

There was no obvious abnormality in the clinical observation of the animals in each dose group of compound 1 during the administration. Compared with the solvent control group, there was no significant difference (p>0.05) in body weight and body weight growth rate between the animals in each dose group, and there was no obvious change in food intake.

No toxicological changes were observed in blood biochemical indicators of Compound 1 in each dose group. Compared with the solvent control group, there were no obvious abnormalities in coagulation function and urine indexes of the animals in each group.

After the last administration, the animals were euthanized after anesthesia, and the autopsy results showed that there were no obvious abnormalities in the gross pathological anatomy of the animals in each dose group of Compound 1.

Compared with the solvent control group, there were no obvious abnormalities in the change of organ coefficient in each drug-administered group. Cardiac histopathological examination showed that in each drug-administered group, there were no obvious lesions in each layer of the ascending aorta wall, no lesions in the coronary artery wall, and no abnormalities in the atrioventricular valve. No obvious abnormalities were observed in the cardiac pathological examination.

5. Conclusion: Compound 1 has good safety under the conditions of this assay.

Therapeutic Effect Assay

Test Example 8. Therapeutic Effect Assay of TGFβ Compound on B16-F1 Xenograft C57 Mice 1. Test Purpose Evaluation of the inhibition effect of the compound of Example 1 on the growth of murine melanoma cell B16-F1 xenograft on C57 mice.

2 Test Drug

Compound 1 was formulated into a 5 mg/ml aqueous solution using 0.5% CMC-Na+0.25% (v/v) Polysorbate 80. The administration concentration was 50 mg/kg, and the oral volume for intragastrical administration was 10 ml/kg.

3. Test Method and Test Material 3.1. Test Animals and Feeding Conditions

Female C57BL/6J mice for laboratory use were purchased from SINO-BRITISH SIPPR/BK LAB. ANIMAL LTD., CO (Shanghai, China, Certificate No.: SCXK (Shanghai) 2008-0016), and the body weight of mice was from 16 to 20 g when purchased. After the animals were purchased, the test was started after 3 days of adaptive feeding. Feeding conditions: SPF grade. Animal feeding method: 12/12 hours light/dark cycle, temperature 23±1° C., humidity 40-50%, the animals were fed with standard sterilized murine feed, and had free access to food and water.

53

3.2. Animal Grouping:

The C57B/6J mice were grouped as follows after adaptive feeding:

| Group | n | Administration mode |
|---|---|---|
| Blank group | 10 | 0.5% CMC (i.g/bid) |
| Compound 1 group | 10 | 50 mg/kg Compound 1 (i.g/bid) |

Note:
bid refers to administration twice a day.

3.3. Test Method

The C57 mice after adaptive feeding were fasted overnight in a metabolic cage, and divided randomly into the following groups after weighing: blank control group and Compound 1 group, 10 mice per group. The skin preparation on the right flank of C57 mice was carried out one day in advance, B16-F1 cells were subcutaneously inoculated (1×10⁶ cells per mouse), and administration was started on the third day after inoculation. Each mouse was intragastrically administrated with Compound 1 (i.g., 10 ml/kg) twice a day, and the blank group was intragastrically administrated with the corresponding solvent. The tumor volume was measured twice a week, the body weight was weighed and the data were recorded.

3.4. Data Statistics

Excel statistical software was used: the average value was calculated by avg; the SD value was calculated by STDEV; the SEM value was calculated as STDEV/SQRT: the difference between the groups P value was calculated by TTEST.

The calculation formula of tumor volume (V) is: $V=\frac{1}{2} \times L_{length} \times L_{short}^{2}$ Tumor inhibition rate (%)=(C−T)/C (%)

Wherein $V_0$ and $V_T$ are the tumor volumes at the beginning of the test and at the end of the test, respectively. C and T are the average tumor volumes of the Blank group and the test group at the end of the test, respectively.

4. Results

The therapeutic effect data of Compound 1 on B16-F1 nude mice xenograft is shown in Table 4.1 and FIG. 1.

Figure 2:
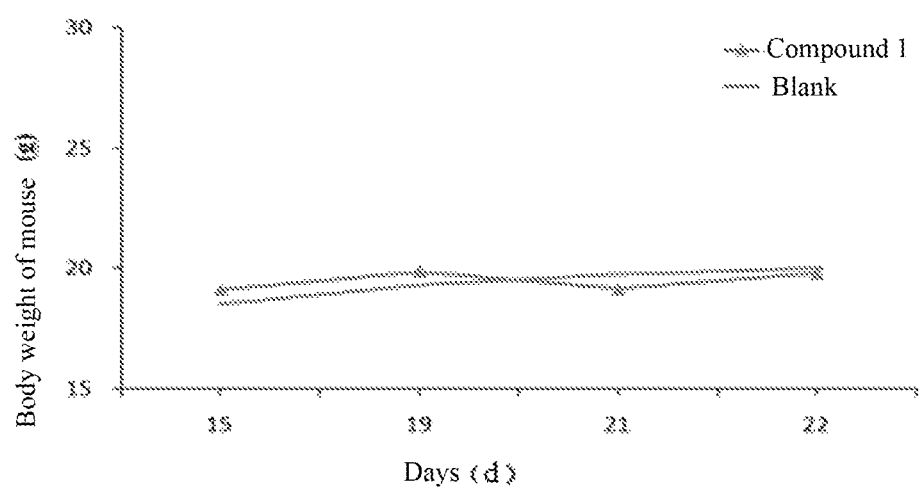
FIG. 2 shows the effect of compound 1 on the body weight of C57 mice.

The effect of Compound 1 on the body weight of C57 mice is shown in FIG. 2.

TABLE 4.1

Therapeutic effect of Compound 1 on B16-F1 nude mice xenograft

| Group | Administration | Route | Average tumor volume (mm³) | | | | % Tumor inhibition rate | p | Number of remaining animals/ |
| | | | d0 | SEM | d22 | SEM | d22 | (vs Blank) | group |
|---|---|---|---|---|---|---|---|---|---|
| Blank | bid/20d | po | 0.00 | 0.00 | 1043.92 | 363.35 | — | — | 10(9) |
| Compound 1 | bid/20d | po | 0.00 | 0.00 | 301.53 | 63.19 | 71.12%* | 0.048921 | 10(10) |

*p < 0.05

5. Conclusion

Compound 1 was administrated on Day 4 after tumor cell transplantation, twice a day. The tumor volume in Compound 1 group was significantly smaller than that in the blank control group on Day 19. The tumor inhibition rate was calculated to be 71.12%, and the administration had no effect on the body weight of the mice.

54

What is claimed is:

1. A compound of formula (I):

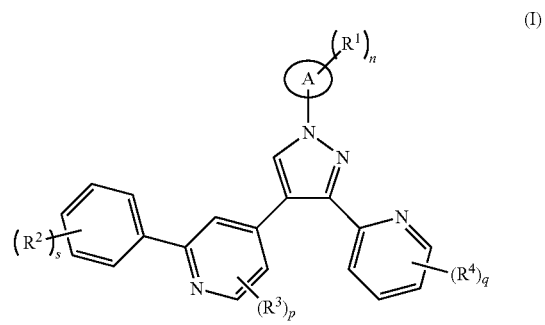

or a tautomer, mesomer, racemate, enantiomer, diastereomer thereof, or mixture thereof, or a pharmaceutically acceptable salt thereof, wherein:

ring A is $C_3$-$C_6$cycloalkyl or 3 to 6 member heterocyclyl;

each $R^1$ is identical or different and each is independently selected from the group consisting of hydrogen, halogen, $C_{1-6}$alkyl, $C_{1-6}$alkoxy, $C_{1-6}$haloalkyl, hydroxy, hydroxy$C_{1-6}$alkyl, cyano, amino, nitro, —S(O)$_m$R$^5$ and —C(O)OR$^5$;

each $R^2$ is identical or different and each is independently selected from the group consisting of hydrogen, halogen, $C_{1-6}$alkyl, $C_{1-6}$alkoxy, $C_{1-6}$haloalkyl, hydroxy, hydroxy$C_{1-6}$alkyl, cyano, amino, nitro, —C(O)R$^5$ and —S(O)$_m$R$^5$;

each $R^3$ is identical or different and each is independently selected from the group consisting of hydrogen, halogen and $C_{1-6}$alkyl;

each $R^4$ is identical or different and each is independently selected from the group consisting of hydrogen, halogen, $C_{1-6}$alkyl, $C_{1-6}$haloalkyl, hydroxy, hydroxy$C_{1-6}$alkyl, cyano, amino and nitro;

$R^5$ is selected from the group consisting of hydrogen and $C_{1-6}$alkyl;

n is 0, 1 or 2;

s is 0, 1, or 2;

p is 0, 1;

q is 0, 1, or 2; and m is 1 or 2.

2. The compound of formula (I) according to claim 1, being a compound of formula (II):

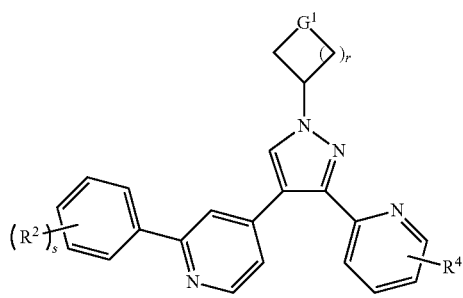

(II)

or a tautomer, mesomer, racemate, enantiomer, diastereomer thereof, or mixture thereof, or a pharmaceutically acceptable salt thereof, wherein:

$G^1$ is $CH_2$, $NR^8$ or O;

$R^8$ is selected from the group consisting of $-S(O)mR^5$, $-C(O)OR^5$, hydrogen and $C_{1-6}$alkyl;

$R^2$, $R^4$ and $R^5$ are as defined in claim 1;

s is 0, 1 or 2;

m is 1 or 2; and r is 0, 1, 2 or 3.

3. The compound of formula (I) according to claim 1, wherein $R^2$ is selected from the group consisting of cyano, $-C(O)R^5$ and $-S(O)mR^5$, $R^5$ $C_{1-6}$alkyl.

4. The compound of formula (I) according to claim 1, wherein $R^4$ is $C_{1-6}$alkyl.

5. The compound according to claim 1, selected from the group consisting of:

1

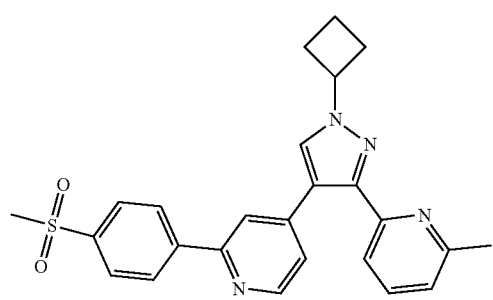

2

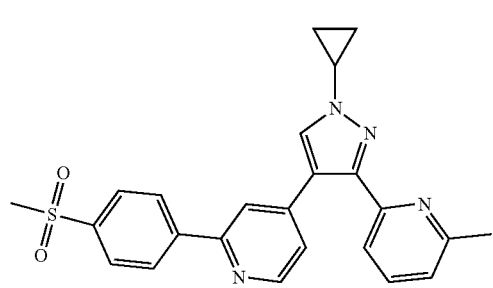

3

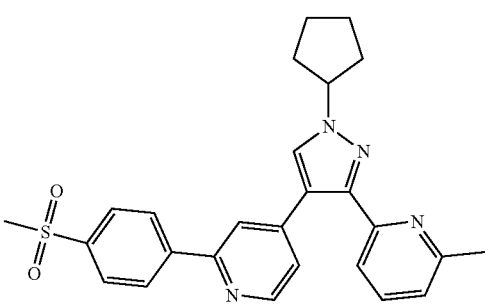

4

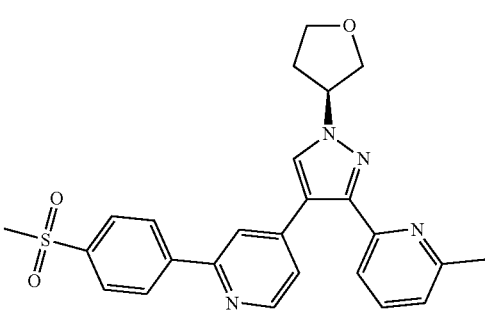

5

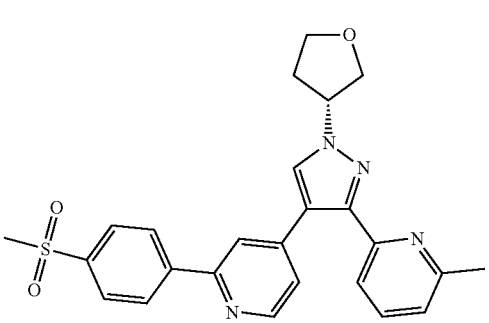

6

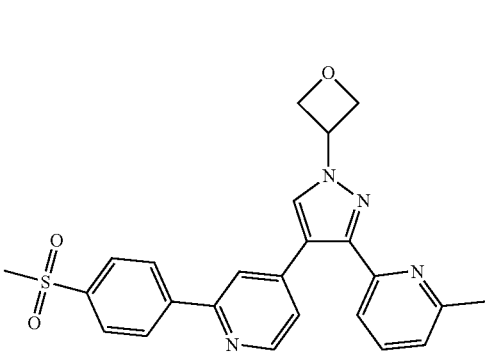

7

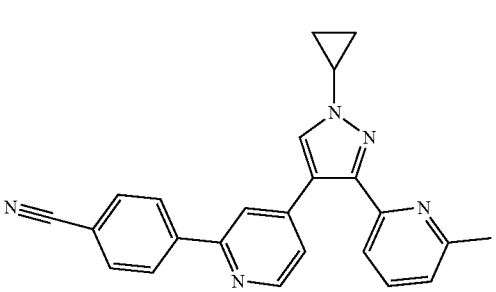

-continued
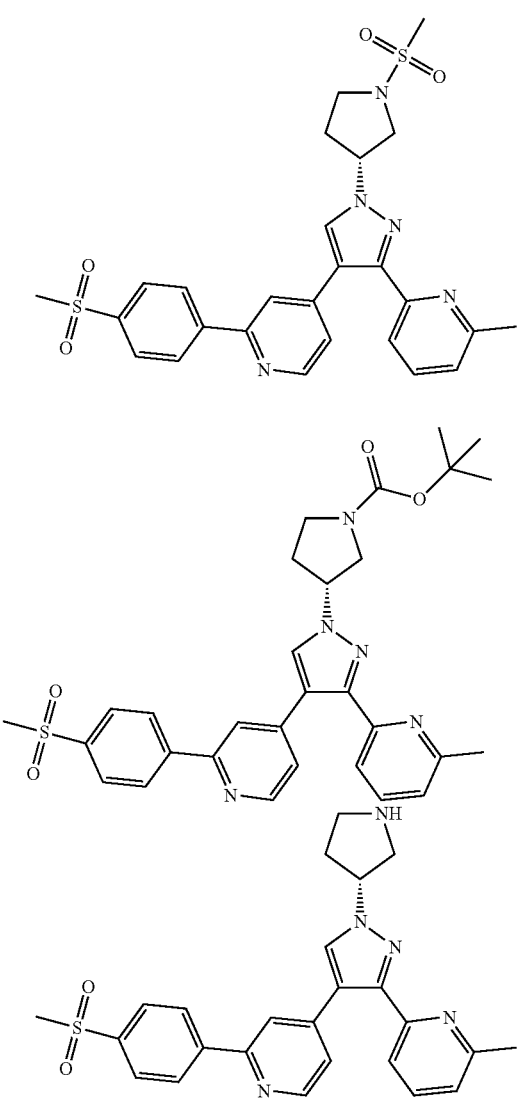
6. A compound of formula (I-A):
(I-A)
or a tautomer, mesomer, racemate, enantiomer, diastereomer thereof, or mixture thereof, or a pharmaceutically acceptable salt thereof,
wherein:
X is halogen, and preferably bromine;
ring A, $R^1$, $R^4$, n and q are as defined in claim 1.
7. The compound of formula (I-A) according to claim 4, selected from the group consisting of:
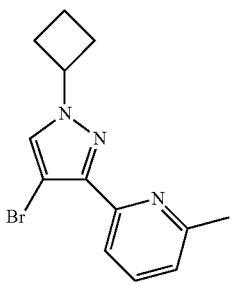
1h
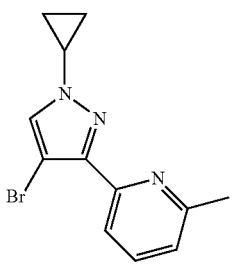
2c
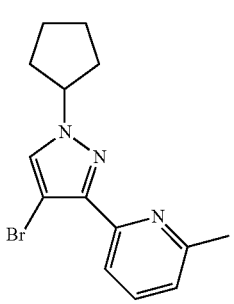
3d
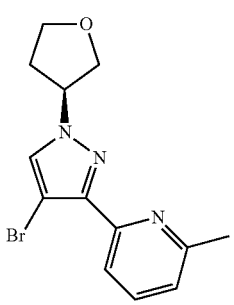
4c
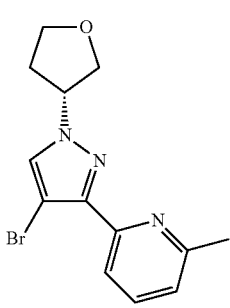
5c
and

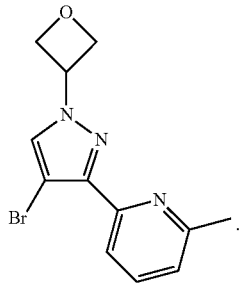

6c

8. A method for preparing the compound of formula (I) according to claim 1, comprising a step of:

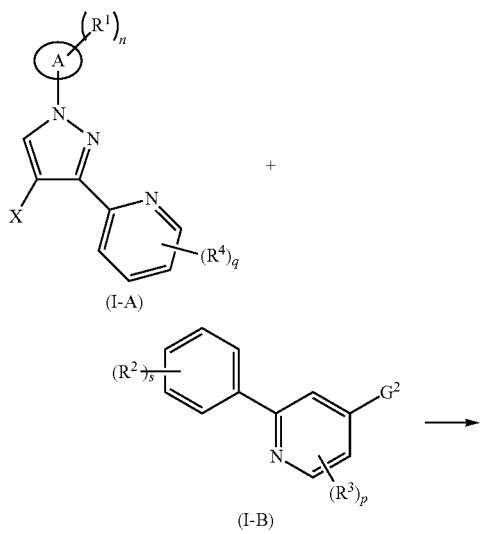

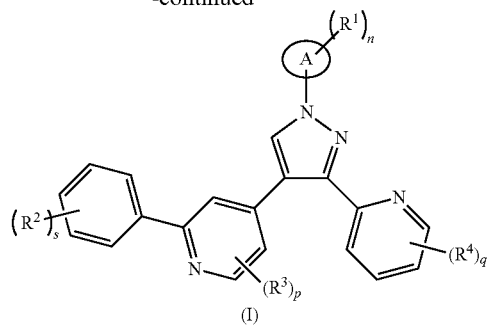

subjecting a compound of formula (I-A) and a compound of formula (I-B) to a Suzuki reaction under an alkaline condition in the presence of a catalyst to obtain the compound of formula (I), wherein:

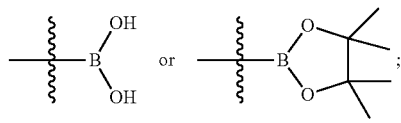

$G^2$ is

X is halogen, and preferably bromine;

ring A, $R^1$~$R^4$, n, s, p and q are as defined in claim 1.

9. A pharmaceutical composition, comprising a therapeutically effective amount of the compound of formula (I), or a tautomer, mesomer, racemate, enantiomer, diastereomer thereof, or mixture thereof, or a pharmaceutically acceptable salt thereof according to claim 1, and one or more pharmaceutically acceptable carriers, diluents or excipients.

10. The compound of formula (I) according to claim 3, wherein $R^2$ is selected from the group consisting of cyano or methanesulfonyl, and s is 1.

* * * * *